United States Patent [19]
Dietrich et al.

[11] Patent Number: 6,040,185
[45] Date of Patent: Mar. 21, 2000

[54] GENETIC STABILIZING ELEMENTS

[75] Inventors: Paul S. Dietrich, Palo Alto, Calif.; Martinus Quirinus Joseph Marie Van Grinsven; Johannes Jacobus Ludgerus Gielen, both of Enkhuizen, Netherlands; Johannes Maria de Haas, Bovenkarspel, Netherlands; Roeland Van Driel, Castricum, Netherlands

[73] Assignee: Novartis AG, Basel, Switzerland

[21] Appl. No.: 08/713,569

[22] Filed: Sep. 11, 1996

Related U.S. Application Data

[63] Continuation of application No. 08/439,156, May 11, 1995, abandoned, which is a continuation of application No. 08/309,819, Sep. 21, 1994, abandoned, which is a continuation-in-part of application No. 08/049,564, Apr. 19, 1993, abandoned.

[30] Foreign Application Priority Data

Apr. 18, 1994 [WO] WIPO ............... PCT/EP94/01193

[51] Int. Cl.$^7$ ............... C12N 15/29; C12N 15/82
[52] U.S. Cl. ............... 435/468; 435/320.1; 536/23.6; 536/24.1; 800/278
[58] Field of Search ............... 536/23.6, 24.1; 435/172.3, 320.1, 468; 800/278

[56] References Cited

U.S. PATENT DOCUMENTS 5,187,267 2/1993 Comai et al. ............... 536/27

FOREIGN PATENT DOCUMENTS 0338 266 10/1989 European Pat. Off. .
94 07902 4/1994 WIPO .

OTHER PUBLICATIONS

Stoilov, L.M. et al., (1992), Plant Cell Reports, 11:355–358.
Hudspeth, R.L. and J.W. Grula, (1989), Plant Molecular Biology, 12:579–589.
Bowen. Brian C., (1981), Nucleic Acids Research, 9:(19):5093–5108.
DeBlock, M. et al., (1984), EMBO Journal, 3 (8) 1681–1689.
Gasser, S.M., (1988) Architecture of Eukaryotic Genes: Symposium on Chromatin Structure of Plant Genes, Frankfurt am Main, W. Germany, Sep., 1986, XIV t 518, P. VCH Publishers, N.Y. pp. 461–471.
Phi–Van, L. et al., (1990), Mol. Cell. Biol., 10:2302–2307.
Eissenberg, J.C. and Elgen, S.C.R. (1991) Trends in Genetics, 7:335–340.
Hall, G. et al., (1991), Proc. Nat. Acad. Sci. USA 88:9320–9324.
Slatter. R.E., et al., (1991) Plant Cell,, 3:1239–1250.
Breyre, P. et al., (1992) Plant Cell, 4:463–471.
van Driel, R. et al., (1991), J. Cell. Biochem., 47:1–6.
Schoffl, F. et al., (1991), 3rd Intl. Cong. Soc. of Plant. Mol. Biol., Poster Abstract No. 407.
Schoffl, F. et al., (1993), Transgeneic Research, 2:93–100.
Childs, L.C., et al., (1992), Biological Abstracts/RRM, No. BR 44:6469.
Schoffl, F. et al., (1993), Chemical Abst. 118:(23) Abstract No. 227377.
Kleim, M. et al., (1991), Biological Absts., BR42:28037.
Ott, R.W. et al., (1990), Mol. Gen. Genet. 221: 121–124.
Mlynarova, L. et al., (1994), Plant Cell, 6:417–426.
Meyer. P. et al. (1988), Proc. Natl. Acad. Sci., USA, 85:8568–8572.
Marchesi, M.L. et al., (1989), Theor. Appl. Genet. 78:113–118.
Childs, L.C. et al., (1993), Biochem Gentics, 118:301.
Zabel, P. et al., (1986), Chem. Abst. vol. 104, No. 9, No. 63286.
Stief, Aribert et al., "A nuclear DNA attachment element mediates elevated and position–independent gene activity" Nature 341 (343–345) 1989.
Elgin, S.C.R. "Chromatin structure and gene activity" Current Opinion, Cell Biology 2 (437–445) 1990.

*Primary Examiner*—David T. Fox
*Attorney, Agent, or Firm*—Tom Hoxie

[57] ABSTRACT

Disclosed is a stabilized gene for transforming a host plant cell said gene comprising a gene exogenous to the plant cell and at least one stabilizing DNA segment in a 3'- or 5'-flanking region to said exogenous gene. Additionally, the invention relates to vectors comprising at least one stabilizing DNA segment in a 3'- or 5'-flanking region to the exogenous gene and methods for transforming plant cells. These stabilizing DNA segments include MAR, SAR, LCR, or LAR, HR and other repetitive elements.

14 Claims, 5 Drawing Sheets

SEQUENCE LISTING

```
(1) GENERAL INFORMATION:

(iii) NUMBER OF SEQUENCES: 8

(2) INFORMATION FOR SEQ ID NO: 1:

(i) SEQUENCE CHARACTERISTICS:
          (A) LENGTH: 1354 base pairs
          (B) TYPE: nucleic acid
          (C) STRANDEDNESS: double
          (D) TOPOLOGY: unknown (ii) MOLECULE TYPE: DNA (genomic)

(iii) HYPOTHETICAL: NO (iii) ANTI-SENSE: NO (vi) ORIGINAL SOURCE:
          (A) ORGANISM: Zea mays (xi) SEQUENCE DESCRIPTION: SEQ ID NO: 1:

GAATTCTTAT CGATACTGGA ACTCAGAGCA TAGGGGGGAA AGTCGATTTA TGGATGGAAT     60

CAAATACGCA GTATTTACAG AAAAGAGTCT TCGTTTATTG GGAAAGAATC AATATACTTT    120

TAATGTCGAA TCGGGATTCA CTAAGACAGA AATAAAGCAT TGGGTCGAAC TCTTCTTTGG    180
```

```
TGTTAAGGTA GTAGCTGTGA ATAGCCATCG ACTACCCGGA AAGGGTAGAA GAATGGGACC      240

TATTCTGGGA CATACAATGC ATTACAGACG TATGATCATT ACCCTTCAAC CGGGTTATTC      300

TATTCCACTT CTAGATAGAG AACGAACTAA AGGAGAATAC TTAATAATAC GGCGAAACAT      360

TTATACAAAA CACCTATCCC GAGCACACGC AAGGGAACCG TAGACAGGCA AGTGAAATCC      420

AATCCACGAA ATAAATTGAT CCATGGACGG CACCGTTGTG GTAAAGGTCG TAATGCCAGA      480

GGAATCATTA CCGCAAGGCA TAGAGGGGGA GGTCATAAGC GCCTATACCG TAAAATCGAT      540

TTTCGACGGA ATCAAAAAGA CATATCTGGT AGAATCATAA CCATAGAATA CGACCCTAAT      600

CGAAATGCAT ACATTTGTCT CATACACTAT GGGGATGGTG AGAAGAAGAT ATATTTTACA      660

TCCCAGAGGG GCTATAATTG GAGATACTAT TGTTTCTGGT ACAAAAGTTC CTATATCAAT      720

GGGAAATGCC CTACCTTTGA GTGCGGTTTG AACTATTGAT TTACGTAATT GGAAGTAACC      780

AATTAGGTTT ACGACGAAAC CTAGAAATCG ATCACTGATC CAATTTGACT ACCTCTACGG      840

GATAGACCTC AACAGAAAAC TGTTGAGTAA CGGCAGCAAG TGATTGAGTT CAGTAGTTCC      900

TCATAGAAAA TTATTGACTC TAGAGATATG GTAAATATGGA GAAGACAAAA TTGTTTGAAG      960

CACGCACAGA ACCGGAAGCG CCCCTTGTTT CAAAGAGAGG AGGACGGGTT ATTCACATTT     1020

AATTTGATGG TCAGAGGCGA ATTGAAAGTT AAGCAGTGGT AATTAAGACC CCCGGGTGAA     1080

AATAGGGATG TCTCCTACGT TACCCATAAT ATGTGGAAGT ATCGACGTAA TTTCATAGAG     1140

TCATTCGATC TGAATGCTAC ATGAAGAACA TAAGCCAGAT GACGGAACGC GGAGACCTAG     1200

GATGTAGAAG ATCATAACAT GAGCGATTCG GCGGATTTGG ATTCCTTTTC TATATATCCA     1260

CTCATGTGGT ACTTCATCAT ACGATTCATA TAAGATCCAT CTGTCTAGAG ATCGTCATAT     1320

ACATCTAGAA AGCCGTATGC TTTGGAAGAA GCTT                                 1354

(2) INFORMATION FOR SEQ ID NO: 2:

(i) SEQUENCE CHARACTERISTICS:
        (A) LENGTH: 1673 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:
         (A) ORGANISM: Zea mays (xi) SEQUENCE DESCRIPTION: SEQ ID NO: 2:

GAATTCTGTG GAAAGCCGTA TTCGATGAAA GTCGTATGTA CGGCTTGGAG GGAGATCTTT       60

CCTATCTTTC GAGATCCACC CTACAATATG GGGCCAAAAA GCCAAAAAAA TAAGTGATTC      120

GTTTTTAGCC CTTATAAAAA GAAAACGGAT TCTTGAACCT CTTTCACGCT CATGTCACGT      180

CGAGGTACTG CAGAAAAAAG AACCGCAAAA TCCGATCCAA TTTTTCGTAA TCGATTAGTT      240

AACATGGTGG TTAACCGTAT TATGAAAGAC GGAAAAAAAT CATTGGCTTA TCAAATTCTC      300

TATCGAGCCG TGAAAAAGAT TCAACAAAAG ACAGAAACAA ATCCACTATT GGTTTTACGT      360

CAAGCAATAC GTAGAGTAAC TCCCAATATA GGAGTAAAAA CAAGACGTAA TAAAAAGGA      420

TCGACGCGGA AAGTTCCGAT TGAAATAGGA TCTAAACAAG GAAGAGCACT TGCCATTCGT      480

TGGTTATTAG AAGCATCCCA AAAGCGTCCG GGTCGAAATA TGGCTTTCAA ATTAAGTTCC      540
```

```
GAATTAGTAG ATGCTGCCAA AGGGAGTGGG GGTGCCATAC GCAAAAAGGA AGCGACTCAT      600

AGAATGGCAG AGGCAAATAG AGCTCTTGCA CATTTTCGTT AATCCATGAA CAGAATCTAG      660

GTATGTAGAC ACATGGATCC ATACATCTCG ATCGGAAAAG AATCAATAGA AGGAGAATCG      720

GACGATATCT TTTTCGAAAC AAATAAAAAG GAAAAAAAAG AGAAAACAGA AATCATGATC      780

AACTAAGCCT CTCGGGGGCT TGCTTAAGAA TAAGAAAGAG GAATCTTATG GAAATAGCAT      840

GGAATAAGGT TTGATCCTAT TCATGGGGAT TCCGTAAATA TCCCATTCCA AAAATCGAAA      900

CAATCGGGAC TTTTCGGAGA TTGGCTGCAG TTACTAATTC ATGATCTGGC ATGTACAGAA      960

TGAAAACTTC ATTCTCGATT CTACGAGAAT TTTTATGAAA GCGTTTCATT TGCTTCTCTT     1020

CCATGGAAGT TTCATTTTCC CAGAATGTAT CCTAATTTTT GGCCTAATTC TTCTTCTGAT     1080

GATCGATTTA ACCTCTGATC AAAAAGATAG ACCTTGGTTC TATTTCATCT CTTCAACAAG     1140

TTTAGTAATA AGCATAACGG CCCTATTGTT CCGATGGAGA GAAGAACCTA TAATTAGCTT     1200

TTCGGGAAAT TTCCAAACGA ACAATTTCAA CGAAATCTTT CAATTTCTTA TTTTATTATG     1260

TTCAACTTTA TGTATTCCTC TATCCGTAGA GTACATTGAA TGTACAGAAA TGGCTATAAC     1320

AGAGTTTCTG TTATTCGTAT TAACAGCTAC TCTAGGGGGA ATGTTTTTAT GTGGTGCTAA     1380

CGATTTAATA ACTATCTTTG TAGCTCCAGA ATGTTTCAGT TTATGTTCCT ACCTATTGTC     1440

TGGATATACC AAGAGAGATC TACGGTCTAA TGAGGCTACT ATGAAATATT TACTCATGGG     1500

TGGGGCAAGC TCTTCTATTC TGGTTCATGG TTTCTCTTGG CTATATGGTT CATCTGGGGG     1560

GGAGATCGAG CTTCAAGAAA TTGTGAATGG TCTTATCAAT ACACAAATGT ATAACTCCCC     1620

AGGAATTTCA ATTGCGCTTA TATTCATCAC TGTAGGACTT GGGTTCAAGC TTU           1673

(2) INFORMATION FOR SEQ ID NO: 3:

(i) SEQUENCE CHARACTERISTICS:
        (A) LENGTH: 1353 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:
         (A) ORGANISM: Zea mays (xi) SEQUENCE DESCRIPTION: SEQ ID NO: 3:

AAGCTTCTTC CAAAGCATAC GGCTTTCTAG ATGTATATGA CGATCTCTAG ACAGATGGAT       60

CTTATATGAA TCGTATGATG AAGTACCACA TGAGTGGATA TATAGAAAAG GAATCCAAAT      120

CCGCCGAATC GCTCATGTTA TGATCTTCTA CATCCTAGGT CTCCGCGTTC CGTCATCTGG      180

CTTATGTTCT TCATGTAGCA TTCAGATCGA ATGACTCTAT GAAATTACGT CGATACTTCC      240

ACATATTATG GGTAACGTAG GAGACATCCC TATTTTCACC CGGGGGTCTT AATTACCACT      300

GCTTAACTTT CAATTCGCCT CTGACCATCA AATTAAATGT GAATAACCCG TCCTCCTCTC      360

TTTGAAACAA GGGGCGCTTC CGGTTCTGTG CGTGCTTCAA ACAATTTTGT CTTCTCCATA      420

TTACCATATC TCTAGAGTCA ATAATTTTCT ATGAGGAACT ACTGAACTCA ATCACTTGCT      480

GCCGTTACTC AACAGTTTTC TGTTGAGGTC TATCCCGTAG AGGTAGTCAA ATTGGATCAG      540

TGATCGATTT CTAGGTTTCG TCGTAAACCT AATTGGTTAC TTCCAATTAC GTAAATCAAT      600

AGTTCAAACC GCACTCAAAG GTAGGGCATT TCCCATTGAT ATAGGAACTT TTGTACCAGA      660
```

-continued

```
AACAATAGTA TCTCCAATTA TAGCCCCTCT GGGATGTAAA ATATATCTCT TCTCACCATC      720

CCCATAGTGT ATGAGACAAA TGTATGCATT TCGATTAGGG TCGTATTCTA TGGTTATGAT      780

TCTACCAGAT ATGTCTTTTT GATTCCGTCG AAAATCGATT TTACGGTATA GGCGCTTATG      840

ACCTCCCCCT CTATGCCTTG CGGTAATGAT TCCTCTGGCA TTACGACCTT TACCACAACG      900

GTGCCGTCCA TGGATCAATT TATTTCGTGG ATTGGATTTC ACTTGCCTGT CTACGGTTCC      960

CTTGCGTGTG CTCGGGATAG GTGTTTTGTA TAAATGTTTC GCCGTATTAT TAAGTATTCT     1020

CCTTTAGTTC GTTCTCTATC TAGAAGTGGA ATAGAATAAC CCGGTTGAAG GGTAATGATC     1080

ATACGTCTGT AATGCATTGT ATGTCCCAGA ATAGGTCCCA TTCTTCTACC CTTTCCGGGT     1140

AGTCGATGGC TATTCACAGC TACTACCTTA ACACCAAAGA AGAGTTCGAC CCAATGCTTT     1200

ATTTCTGTCT TAGTGAATCC CGATTCGACA TTAAAAGTAT ATTGATTCTT TCCCAATAAA     1260

CGAAGACTCT TTTCTGTAAA TACTGCGTAT TTGATTCCAT CCATAAATCG ACTTTCCCCC     1320

CTATGCTCTG AGTTCCAGTA TCGATAAGAA TTC                                  1353
```

(2) INFORMATION FOR SEQ ID NO: 4:

(i) SEQUENCE CHARACTERISTICS:
        (A) LENGTH: 862 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:
        (A) ORGANISM: Zea mays (xi) SEQUENCE DESCRIPTION: SEQ ID NO: 4:

```
GAATTCAGGT AATCCCGTCG GCCCAAAACC GACGGGAATT AATAGTCGGA GTTTAGTTAA       60

TTCTCGTAGG TAGCTGATGG GAATTAGTAA TTCCCGTCGG TTTACGCGCA GTCGACATGA      120

ATTAATTAGT CAATTCCCGT CAACCAGTTA ATTTCTGTCG GACACGTCTG ACCCATGGGA      180

ATTATTCGAC GAGGTAATCC AAATCCACGA GGTCTTTGTA ACAATTAATA GAGAATGCAA      240

ACTTGGACTT GATTGACATC AGCTGGGTCA CGAAATCGAG AACGGTCACA TCAGTGTGCT      300

CATGAAGAGG CTCTTTTGAC GCTTTGAGGA GGTCAAAGAA CTTCTGAACC TCCCGGTGTA      360

GTGAATCATG ATGATATGGG GCCAATTTCG ACTGCAAATC CACAAGCATC CGCCTAATAT      420

TATATATTTG TGACAAAGCA ATTGCATGGT TTAGAAACAT CTGAGTTTTG GCAAACCATT      480

CACTTGTGTG ACACCCACCC TTTTTGAAAC CTTCATACAT CCAATCACGT CTATCACCCA      540

TTATTGCGGC TGTGTACAAG TAAGAAGTGT GTGTGAGACA TTCATATTTC CTACACATCA      600

CACATAACAT GTATGGTACA TACATGTGAT GCATAGCGGT CTGAAATGAG TGACACATAG      660

TTTGCAAAAC TATATATGTA GTTGTGAAAG GGAAATAGTC TCAACATTTC CTATAATCGA      720

TTTGGGTGTT TGACGACCAT AACAAACCTT GTGGACTAAC CAGTTTGTCT AGTTGATCAT      780

TCCACAGGTG CATAAGTTCA TCTACAACTA TTCTAAATCG ACTATCCAGA ATACCGTAGA      840

TTATTTCGGA CAGGAGAAGC TT                                              862
```

(2) INFORMATION FOR SEQ ID NO: 5:

(i) SEQUENCE CHARACTERISTICS:

(A) LENGTH: 1268 base pairs
(B) TYPE: nucleic acid
(C) STRANDEDNESS: double
(D) TOPOLOGY: unknown (ii) MOLECULE TYPE: DNA (genomic)

(iii) HYPOTHETICAL: NO (iii) ANTI-SENSE: NO (vi) ORIGINAL SOURCE:
(A) ORGANISM: Zea mays (xi) SEQUENCE DESCRIPTION: SEQ ID NO: 5:

```
AAGCTTCCAA TCTCTCCAAG TTCCACAACT GAGACAAGTG ATCATTAGTG ATTATAGACT      60
TGAGAGAGAG AGAGAGTGAT CCGTGTATTA TTTATCGCTC TTGTTGCTTG GCTTTTGCAA     120
TCGTGCTTTC TTCTATTCCC ATTCTTATTC TCAAGTGACT TGTAATCAAA GAAAGAGACA     180
CCAAGTGTGG GGTGGTCCTT GTGGGTCTA AGTGACCCGG TTGATTAAGG AGAAAGCTCA      240
GTCGGTCTAG GTGGCCGTTT GAGAGAGGGA AAGGGTTGAA AGAGACCCGG TCTTTGTGAC     300
CACCTCAACG GGGACTAGGT TCTTTGGAAC CGAACCTCGG TAAAACAAAT CACCGTGTCA     360
TCCGCTTTAT TTCTTGGTTG ATTTGTTTTC GCCCTCTCTC CTAGACTTGG ATTTTATTCT     420
AACGCTAACC CCGGCTTGAA GTGTGCTTAA AGTTTGTAAA TTTCAGTTTC CGCCTATCCA     480
CCCCCCTCTA GGCGACTTTC AAGTTGCAAC AATGAGGTAG TAGAATCAAT ACTTANATAA     540
CATGACATTA ATCANTTAAC AATATTCANA ACGAATTAAT AATTTGCAAC AATTACTAGG     600
TGTATAACAA CACAGTCACC ATCAAAATTC ATCAACTAAT AACATCAAGC CACATAGTTT     660
ATATTTGCAA CATAAATATA AAAATAGCAA CTACAATGTA TAAAGTCATA TTAAGACTAA     720
TAACACTATC AATTAACAAA TTTAAGATAA CTATAATTGC ATAAAAGTTA ACTCTCGTCG     780
GTCACAAAAA ACTGACGAAA ATAAATGTCT TAATATATAT ATTAAGCACC TCTAATTAAT     840
CACACTTTCA TTTGTATCGC ATAGGTCTAG GATTATACCT CGACGACTCG AATGACGTTG     900
TCCCGTGGAG GAGCTTGTGT AGGCCGGATG GCAGCACAGA CGGTGGTCGT TGGAGGAGAT     960
TGCGAGGGCC GATGGGGGGG CGTGGTGGCC GCGGTAGTGG GCAGTCCCAA CAATGTGGCA    1020
GTCACGGTTG GCGCCGGCGA TGGGCGTACC GCGGTGGGCA GTCCCGACGG CGTGGCAGTG    1080
NCGGTGGGCG CCGGCGACAG GCGGACCTCC AATGGCGGAC GACGTTGGGG CGGCCAGGCG    1140
GAGGGCGGTG GCAGTGGGCG TAGGGCGACG ACGGGGGACA GACCGGACCG GCGACGACGA    1200
CGTTGAAGAA AATGTTGCGG TTTGAAAATG AGCCCGTGCG GGGGATAGAC CGCGCCTCAT    1260
AAAAGCTT                                                            1268
```

(2) INFORMATION FOR SEQ ID NO: 6:

(i) SEQUENCE CHARACTERISTICS:
(A) LENGTH: 399 base pairs
(B) TYPE: nucleic acid
(C) STRANDEDNESS: double
(D) TOPOLOGY: unknown (ii) MOLECULE TYPE: DNA (genomic)

(iii) HYPOTHETICAL: NO (iii) ANTI-SENSE: NO (vi) ORIGINAL SOURCE:
(A) ORGANISM: Zea mays (xi) SEQUENCE DESCRIPTION: SEQ ID NO: 6:

```
GTAACTAGCA AGTTCAGAGC ATCATTTAAG TAATTAAAAG AAAAAATATT AAATATATAA        60

ATCATAAGAT GATATCAAAA AATTCATGAA CAGTCTCTTC ATTTTTTTTC AATAAAAATA       120

TTTTTATTTT AATTTTTTAA AATAATATCC TCATAACATT GGTTTAACTC CCAAGTTTAA       180

AATTTACTAG TGCTAGATAA ATTCTCTAAG ATAATGTATA GATAAAAATA AGATAAATTA       240

GAAAATTTTT AAGGAGAGAT TTTTTTTTAT AAAAATTAGG TATATGTATT GGTTTTAGTT       300

TACAGAGAAA TATAATTTAT ATTTTCTTTT TGTGTAAATA TTAATGAAAA AAATTATTCA       360

AATTCAATCT AAATCTTAAT ATTTTTTTTG ACAGAATCC                              399

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:
        (A) ORGANISM: synthetic (xi) SEQUENCE DESCRIPTION: SEQ ID NO: 7:

TGAGGAATTC GCGGTCTATC CCCCGCACG                                          29

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:
        (A) ORGANISM: synthetic (xi) SEQUENCE DESCRIPTION: SEQ ID NO: 8:

GTCGGAATTC AAGTTCCACA ACTGAGACAA G                                       31
```

GENETIC STABILIZING ELEMENTS

This is a CONTINUATION of application Ser. No. 08/439,156, filed on May 11, 1995, now abandoned, which is a CONTINUATION of application Ser. No. 08/309,819, filed on Sep. 21, 1994, now abandoned, which is a CONTINUATION-IN-PART of application Ser. No. 08/049,564, filed Apr. 19, 1993, now abandoned.

FIELD OF THE INVENTION

The invention relates to the field of plant molecular biology, in particular to the technology of transferring an exogenous gene into a plant cell and conferring a stable phenotype associated with said gene on a transgenic plant.

BACKGROUND OF THE INVENTION

"Transgene" or "exogenous gene" are terms used in the art to denote a gene which has been transferred to a host cell or host plant from a source other than the host cell or host plant. However, a transgene may herein refer to a gene normally locatable in an host plant or plant cell, to which is added one or more flanking regions comprising stabilizing DNA segments. Thus a gene endogenous to a host plant cell or host plant may be modified with flanking regions comprising stabilizing DNA segments whereby the endogenous gene becomes an exogenous gene or transgene with the meaning of the instant application. As used herein, the terms "transgene" and "exogenous gene" have the same meaning. Transfer of an exogenous gene to a host plant cell can be accomplished by a variety of means known in the art. Most classes of plants have been transformed and regenerated to yield adult plants expressing a phenotype associated with the transgene.

The process of producing a transgenic plant typically includes exposing plant cells, which may be in the form of individual cells, protoplasts or excised tissue, to DNA comprising the exogenous gene, in order to introduce the exogenous gene into the host cells. Only a fraction of the cells exposed to the DNA are actually transformed. The recipient cells are then cultured in vitro in order to proliferate the transformants and to identify and select for those which express the transgene. Frequently a selectable marker is introduced, together with the exogenous DNA, so that transformants can be selected by their ability to grow under conditions that inhibit growth of nontransformed cells, or which favor growth of transformed cells. However, it is also possible in some cases to identify directly the transformed cells or callus containing them. Further steps include techniques of regeneration to produce differentiated shoots, roots or embryos from which, ultimately, whole plants can be obtained. For reviews on plant transformation and regeneration, see Crossway, A. et al. (1986) Mol. Gen. Genet. 202:179–185; Horsch, R. B. et al. (1985) Science 227:1229–1231; Gasser, C. S. and Fraley, R. T. (1989) Science 244:1293–1299; Marton, L. et al. (1979) Nature 277:129–131; Klein, T. M. et al. (1988) Proc. Natl. Acad. Sci. USA 85:8502–8505; Krens, F. A. (1982) Nature 296:72–74; Deshayes, A. et al. (1985) EMBO J. 4:2731–2739; Deroles, S. C. and Gardner, R. C. (1988) Plant Mol. Biol. 11:365–377; Czernilofsky, A. P. et al. (1986) DNA 5:101–113; Hain, R. et al. (1985) Mol. Gen. Genet. 199:161–168; Scheerman, S. and Bevan, M. W. (1988) Plant Cell Reports 7:13–16; Shillito, R. D. et al. (1965) Bio/Technology 3:1099–1102; Valvekens, D. et al. (1988) Proc. Natl. Acad. Sci. USA 85:5536–5540.

Primary transformants are those cells or proliferated tissue (e.g., callus colonies) which are initially observable, directly or indirectly, as possessing the exogenous gene after the transformation step. Most commonly, possession of the exogenous gene is observed indirectly as expression of a co-transformed selectable marker. In some instances the phenotype associated with expression of the exogenous gene will be observable in the primary transformant. When a selectable marker is present, such as antibiotic resistance, culture in the presence of the selection agent, the antibiotic, ensures that only cells expressing the resistance phenotype will grow. In the absence of selection, however, it has frequently been observed that descendants of primary transformants lose the phenotype associated with the transgene. For example, explants of a primary transformant callus often fail to display the phenotype of the exogenous gene, in the absence of continued selection pressure. Furthermore, when whole plants are regenerated from transformed tissue or callus, some of the regenerated plants fail to have the phenotype of the exogenous gene, and the same phenomenon is sometimes observed in the progeny of selfed transformed plants. In such cases it has not been established whether the loss of phenotype is due to loss of the exogenous gene itself, or to loss of ability to express the exogenous gene. The loss of phenotype, whatever the mechanism, results in a gradual decline in overall transformation efficiency, i.e., the total number of transformants declines over time with respect to the number of initial transformants. The present invention provides a means for stabilizing transformants against loss of phenotype associated with the exogenous gene, so that higher overall transformation efficiency is obtainable.

Recent studies of the structure of the eucaryotic cell nucleus and the organization of chromatin within the nucleus have led to new techniques for identifying DNA components and nuclear structural components that participate in organizing cellular DNA in the nucleus. Such studies have demonstrated the existence of a complex nuclear matrix which includes structural components remaining after DNAse I digestion and extraction with 2M NaCl (See Gasser, S. M. (1988) Architecture of Eukaryotic Genes: Symposium on Chromatin Structure of Plant Genes, Frankfurt am Main, W. Germany, September 1986, XIV+518, P VCH Publishers; New York, pp. 461–471). The finding that Li-3,5-diiodosalicylate (LIS) extraction removes histone from chromosomal DNA has made it possible to isolate nuclear scaffold by combining LIS extraction with endonuclease digestion. Such procedures leave residual DNA segments bound to the nuclear scaffold. Such DNA segments have been termed scaffold attachment regions (SAR) and matrix associated regions (MAR). Such DNA segments are considered to be functionally similar in nature, independent of how they are obtained. The term MAR is used herein to refer to DNA segments isolated from nuclear scaffold or nuclear matrix preparations after endonuclease treatment.

MARs typically bind reversibly to nuclear matrix or scaffold preparations. Binding is saturable, indicating binding to a limited number of specific sites. MARs can be of any size, however, they are generally of about 1 kb or less in size and are generally AT rich. They do not necessarily share extensive sequence homology, although certain sequence motifs have been observed in some MARs. Many MARs possess a topoisomerase II cleavage site consensus sequence.

MARs are believed to function in vivo as structural attachment points linking chromosomal DNA to structural elements of the nucleus. Models of chromosome structure have been proposed, in which chromosomal regions between two adjacent MARs form a loop of DNA between the anchor points of the MARs. It has been proposed that MAR attachment facilitates transcription of nearby genes, by locating those genes close to nuclear pores or channels where polymerases, transcription factors, substrates, etc., may concentrate. At the same time, anchorage to the nuclear matrix serves to separate or isolate groups of genes on separate chromatin loops, acting as boundary elements to limit the influence of nearby transcription units on one another, commonly called position effects.

The MARs appear to function across species boundaries, although matrix binding specificity may be diminished, for example when using animal MARs in plants. Functional association between MARs and DNA replication has also been implicated in studies showing that some matrix-binding sequences of maize DNA may function as ARS (autonomous replicating sequence) elements in yeast.

Phi-Van, L. et al. (1990) Mol. Cell Biol. 10:2302–2307, compared the effect on reporter gene expression of the presence or absence of MARs flanking an exogenous reporter gene. The MAR sequence was isolated from the chicken lysozyme gene 5' flanking region, the host cells were fibroblasts. Both enhancement of reporter gene activity and reduction of position effects (individual variation of expression level among independent transfectants) were observed if the reporter gene construct included MARs flanking the gene. A review of boundary functions attributable to MARs was published by Eissenberg, J. C. and Elgin, S. C. R. (1991) Trends in Genetics 7:335–340. The authors suggested that MARs function both as insulators when bracketing a gene together with its enhancers, to maintain activity of the enhancers by isolating them from chromosomal position effects, and as barriers when interposed between a gene and an enhancer.

In higher plants, the existence of MARs has been reported by Hall, G et al. (1991) Proc. Natl. Acad. Sci. USA 88:9320–9324. Tobacco MARs (termed SARS therein) were isolated from flanking regions of three root-specific genes. An "endogenous" assay for MARs was disclosed, based on their ability to bind to nuclear scaffold preparations. An "exogenous" assay, based on ability of isolated scaffolds to bind DNA fragments containing MARs, was also disclosed. A scaffold-associated DNA region located downstream of the pea plastocyanin gene was isolated and characterized by Slatter, R. E. et al. (1991) Plant Cell 3:1239–1250. The SAR was linked to a downstream repeated sequence and had a sequence rich in A and T sequences, several topoisomerase II binding sites and several ARS sequences.

Breyne, P. et al. (1992) Plant Cell 4:463–471 used a tobacco-derived SAR to analyze the effect of flanking a reporter gene in transgenic plants, similar to the experiment described by Phi-Van et al. (1990). Qualitatively similar results were obtained showing an effect of a tobacco SAR flanking a transgene on variance of expression among independent tobacco transformants. However, no increase of average expression level was observed. The effect of reducing variance was not observed for constructs containing a mammalian β-globin SAR instead of the tobacco SAR. All effects heretofore observed have related to phenomena occurring within a single generation.

SUMMARY OF THE INVENTION

The basis of the present invention is that there exist certain stabilizing DNA segments which, when introduced together with an exogenous gene into plant host cells, serve to stabilize the exogenous gene from one generation of cells to the other, or from one generation of transgenic plants to another. Stabilization has occurred when the phenotype associated with the exogenous gene (the "transgene phenotype") is retained from one generation to the next at a higher frequency than is observed in the absence of the stabilizing DNA. Since the rate of loss of the transgene phenotype is most apparent by comparison with primary transformants, stabilization is also defined as a reduction of the frequency of loss of the transgene phenotype over one or more generations when compared with the number of primary transformants.

Stabilizing DNA segments include, but are not limited to, MAR and SAR segments as identified by art-known measures of binding with nuclear matrix or scaffold. Stabilizing DNA segments also include certain repeated sequences, locus control regions (LCR), also known as locus activating regions (LAR) and certain other sequences such as DNAse hypersensitive regions (HR). In the absence of binding assays, suitable candidate stabilizing DNA segments can be identified by various structural attributes such as possession of one or more topoisomerase II binding sites, hypersensitivity to DNAse, having high A & T content and ARS consensus sequences. A stabilizing DNA segment can have one or more of these structural features, however, the absence of one or more such features would not rule out the segment as having the stabilizing function.

A functional test is described herein which exploits the property of a stabilizing DNA segment to separate adjacent genes on a vector into independently expressed units. A stabilizing DNA segment interposed between two genes or transcription units oriented in tandem on a vector, effectively prevents the depressed expression of the downstream gene which occurs in the absence of a stabilizing DNA segment between the genes, as disclosed herein.

Also disclosed herein are data showing that loss of transgene phenotype over a number of generations is not the result of transgene loss, but rather the result of ability to express the transgene. Experiments are reported herein showing stabilization of expression over many cell generations by providing the exogenous gene with flanking stabilizing DNA segments.

Accordingly the invention provides vectors for achieving stable transgene expression over many cell generations by providing stabilizing DNA segments in one or both the 3'- and 5'-flanking regions of the transgene. The invention also includes vectors for achieving independent expression of at least two exogenous genes on the same vector by providing a stabilizing DNA segment interposed between the exogenous genes.

Also included as part of the invention is a method for transforming plant cells with an exogenous gene to enhance the stability of the phenotype associated with the exogenous gene, by introducing into the plant cell a vector having at least one stabilizing DNA segment present in a flanking region of an exogenous gene. In a preferred embodiment the vector will possess more than one stabilizing DNA segment such that the exogenous gene(s) lies between the stabilizing DNA elements.

| | |
|---|---|
| - ▣ - | pBR322 vector fragments |
| - ◆ - | Drosophila histone MAR |
| - ■ - | Rat GDH 5' MAR |
| - ◇ - | Homologous tomato MAR |

Each test represents 100 ng labelled tomato MAR per assay.

Figure 4:
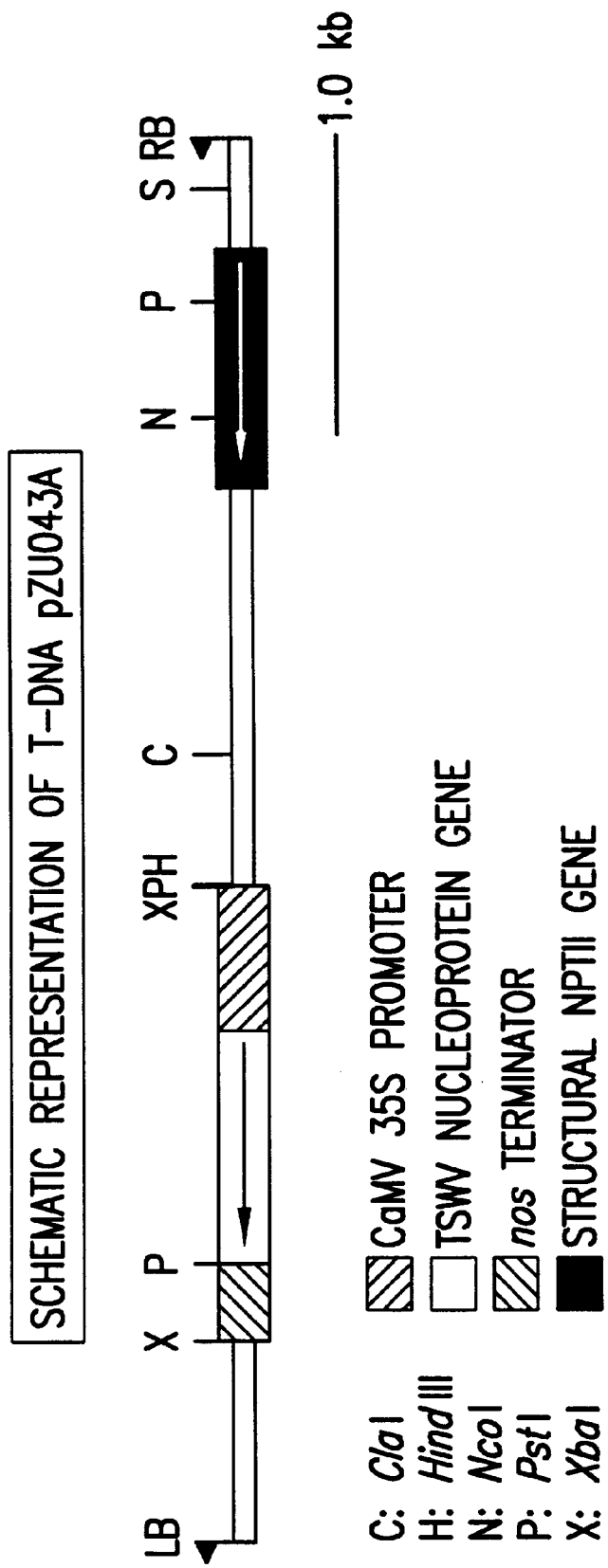

FIG. 4 is a diagram of a T-DNA vector, pZU043A carrying the TSWV nucleoprotein gene controlled by a CaMN 35S promoter. See Example 16.

Figure 5:
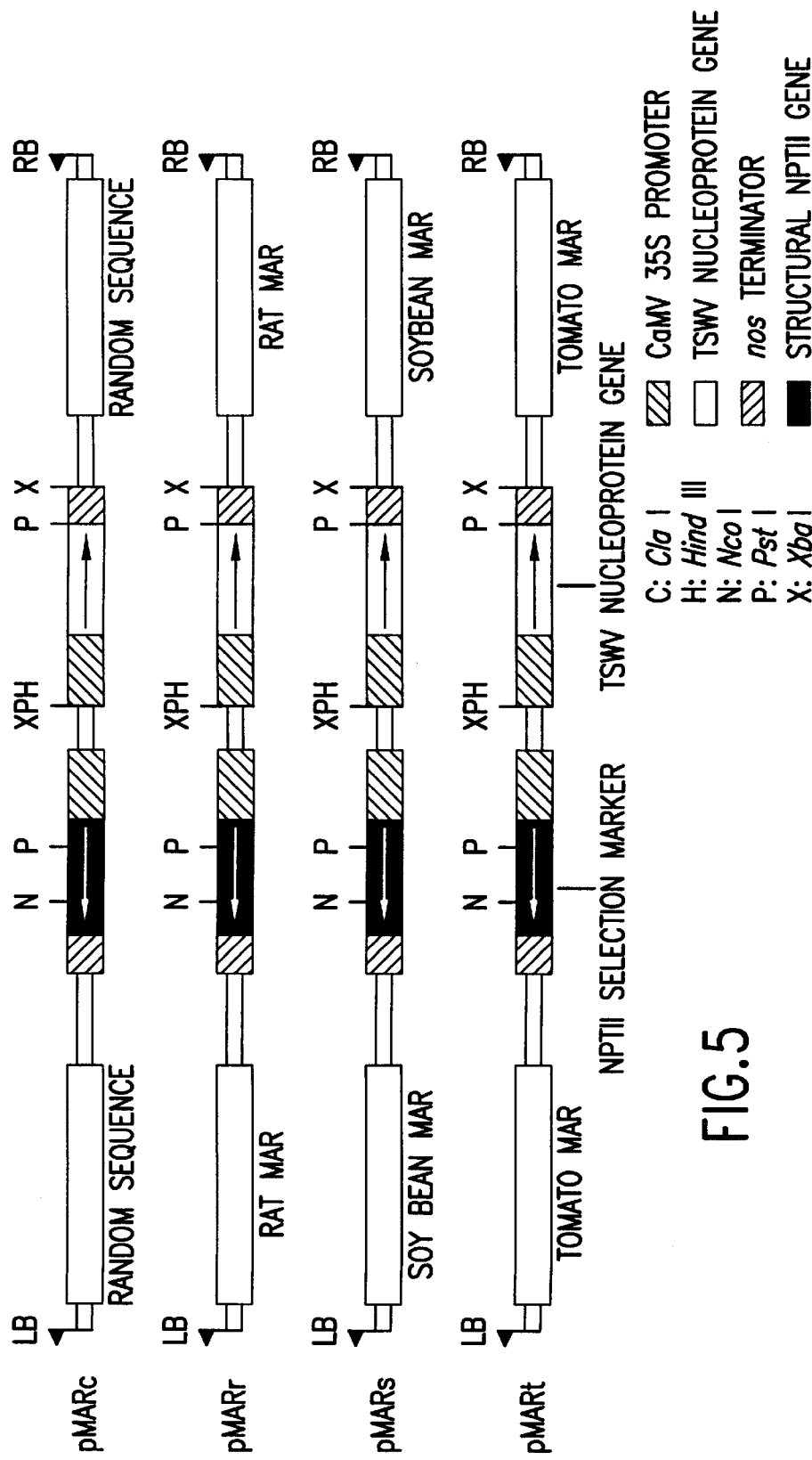

FIG. 5 is a diagram of T-DNA vectors carrying various MAR segments, as described in Example 18.

DETAILED DESCRIPTION OF THE INVENTION

"Stabilization" is the term used herein to denote increased retention of a phenotype associated with an exogenous gene, over one or more plant cell and/or plant generations, when comparing transformants having a "stabilized exogenous gene" of the invention with those having a control exogenous gene. The comparison is made between the number of transformants having a phenotype associated with the exogenous gene ("transgene phenotype") at a given time, and the number of transformants having the transgene phenotype at a later time, after correcting for total cell proliferation. Therefore, it is not the quantitative expression level which is to be measured (although that may incidentally be affected), but the rate of retention of the transgene phenotype itself in individual cell lines and/or plants descendant from primary transformants.

A stabilized exogenous gene is an exogenous gene which includes one or preferably more stabilizing DNA elements in its 3'- and 5'-flanking regions. As it may be the case that more than one exogenous gene is to be introduced to the host plant, it will be recognized that stabilizing DNA elements can be provided such that all genes are flanked, and stabilized by a single pair of stabilizing DNA segments, or they may be individually flanked, or one gene can be flanked while another is left unflanked. In the latter case, the unflanked gene may be less stable than the flanked gene, which may be desired if, for example, the unflanked gene were only useful as a marker for initial transformant selection, but of no value to the whole plant.

Stabilizing DNA segments include MAR, SAR, LCR or LAR, HR and the like as described, supra, repetitive elements as described infra, and other DNA segments sharing structural and functional features therewith. Some stabilizing DNA segments also exert a shielding effect when interposed between two tandemly oriented genes on a single vector, such that the downstream gene is less affected by expression of the upstream gene than would be observed if no stabilizing DNA segment were present. A demonstration of the shielding effect of MRS elements is provided herein, providing a means for recognizing a stabilizing DNA segment. Other means for recognizing a stabilizing DNA segment include the various matrix binding and scaffold binding assays known in the art. Stabilizing DNA elements can be obtained from any eukaryotic or prokaryotic cell type. Preferred sources are eukaryotic cell types from animal or plant sources and most preferred are stabilizing DNA segments compatible with the host cell, such DNA segments may be endogenous to the host cells. Stabilizing DNA segments display a range of effectiveness and specificity. Any detectable level of stabilization is operative, thereby reducing the need to screen and evaluate large numbers of transformants to find satisfactory performers.

Any gene found in or not normally found in the host plant, nor wholly obtained from the host plant, may serve as an exogenous gene. A gene of the host plant modified sufficiently to provide a distinct phenotype qualifies as an exogenous gene. For example, a gene of the host plant provided with a different promoter so that the timing, tissue specificity, expression level, inducibility or other aspect of gene control was altered such that the plant's transgene phenotype was distinct from the wild type, would be an exogenous gene under the definition. The gene of a parasite or pathogen of the host plant or from other sources such as a nonpathogen to the host plant is also an exogenous gene.

The phenotype associated with the exogenous gene, also termed the transgene phenotype herein, is any trait or characteristic conferred on the transgenic plant or host plant cells, by the exogenous gene. A phenotype can range from a measurable amount of the protein or RNA encoded by the exogenous gene, to a physical or agronomic trait. In most cases, more than one phenotype can be detected for a given exogenous gene. For example, where the exogenous gene encodes an insecticidal protein such as the *Bacillus thuringiensis* toxin, the phenotypes include presence of the protein in plant tissues and resistance to certain insects. Where the exogenous gene encodes an antisense RNA to a plant virus, the phenotypes include presence of the RNA in plant tissues and resistance to certain viruses. In some instances, one or more exogenous genes may be introduced in a single stabilized gene cassette, in order to provide an easily measured phenotype linked to a difficultly measurable phenotype. An example is kanamycin resistance linked to a gene for fungal resistance. Therefore, a phenotype associated with an exogenous gene includes a phenotype associated with a linked exogenous gene.

Examples of exogenous genes and their associated phenotypes include, but are not limited to:

a) antisense RNA to confer virus resistance or to modify expression of an endogenous gene of the host plant;

b) viral coat protein and/or RNA, or other viral or plant genes to confer virus resistance;

c) fungus resistance, possibly conferred by a wound induced gene;

d) insect resistance conferred by an insecticidal toxin or other protein;

e) flower color or flower pattern conferred by genes affecting pigment production;

f) yield improvement;

g) drought resistance;

h) self-incompatibility;

i) male sterility j) delayed or accelerated maturation;

k) protein production, for example, conferred by mammalian genes encoding a therapeutically useful protein;

l) improved nutritional balance conferred by a seed storage protein gene modified to affect amino acid balance;

m) herbicide resistance, conferred by various herbicide resistance mechanisms;

n) nitrate tolerance;

o) plant morphology, for example dwarf variety genes that minimize plant resources devoted to vegetative growth;

p) metabolic alterations that increase or modify production of useful plant products such as sugars, starches, complex carbohydrates, oils, alkaloids, gums and the like.

Other sorts of exogenous genes useful for transfer to a plant will be recognized by those skilled in the art as applicable in the present invention.

Construction of transformation vectors incorporating a stabilized exogenous gene is readily accomplished by standard techniques of DNA manipulation. A stabilizing DNA segment can be inserted in the 5'-flanking region upstream of promoter sequences, or in the 3'-flanking region which may or may not lie downstream of polyadenylation signal sequences, if present. The exact distance of the stabilizing DNA segment from either end of the exogenous gene is not critical. However, if the construct includes T-DNA borders of *Agrobacterium tumefaciens*, the stabilizing DNA segments should be inserted so as to be between the T-DNA borders, to ensure integration of the stabilizing DNA segments. The effect of one or more stabilizing DNA elements is to stabilize those genes lying in close association or proximity therewith. Therefore the preferred construction is to place the stabilizing DNA elements so that they flank only the genes whose expression is to be stabilized. Although stabilizing DNA segments do not necessarily have restriction sites at or near their ends, it is a matter of ordinary skill to modify the ends using, e.g., ligation of oligonucleotide linkers, or primers for polymerase chain reaction incorporating a restriction site sequence, to facilitate inserting the stabilizing DNA segments at desired sites on a vector. Orientation of a stabilizing DNA segment with respect to the orientation of the gene to be stabilized is not a critical factor as regards the stabilization function. The stabilizing DNA elements flanking a given gene need not be identical, nor must they be obtained from the same source organism. The stabilizing DNA elements need not be exogenous, but can instead be obtained from the host organism. Although there is superficial similarity between animal MAR and SAR sequences and their plant counterparts, plants are the preferred source for stabilizing DNA element, the most preferred being plants of the host plant species or closely related species.

Stabilizing DNA segments can be isolated by a variety of methods. First, it is possible to analyze the 3' or 5' flanking regions of any stable gene, preferably, but not limited to, those flanking regions lying within about 500 kbp either side of the coding region. Candidates are identifiable by such criteria as DNAse hypersensitivity, topoisomerase II binding sites, ability to bind matrix or scaffold preparations, and the like. An alternative method is simply to clone fragments of a stable gene, then select the fragments that display such properties as DNAse hypersensitivity, locus control regions, matrix binding, scaffold binding and the like. Yet another alternative is to isolate plant nuclei, extract the nuclei with LIS, then treat with an endonuclease including, for example, a restriction endonuclease, extract DNA remaining bound to matrix or scaffold by phenol extraction, and clone the resulting MARs. Another procedure is to isolate plant nuclear matrices or scaffolds, then screen for DNA fragments preferably limited to a size of approximately 0.1–1.0 kb capable of binding to the matrices or scaffolds. Those able to bind tightly are then cloned. As a variation of the foregoing method, an isolated locus control region (LCR) from, e.g., chicken, is used to isolate LCR binding protein. The gene encoding an LCR protein is then cloned and expressed in a suitable system to produce sufficient amounts to be usable to identify plant DNA segments capable of binding to the protein. In every instance where candidate stabilizing DNA segments are cloned, their ability to stabilize a transgene through many cell generations is testable using a marker transgene in a suitable transgenic host plant.

The test host plant preferably displays a low frequency of stable expression in the absence of a stabilizing DNA segment. For example, lettuce displays a frequency of stable expression about 15% of primary transformants, when not transformed with a stabilizing DNA segment.

Transformation can be carried out by any means known in the art. These include, but are not limited to, direct transfer of DNA into whole cells, tissues or protoplasts, optionally assisted by chemical or physical agents to increase cell permeability to DNA, e.g., treatment with polyethylene glycol, dextran sulfate, electroporation and ballistic implantation of DNA-coated particles. Transformation is also mediated by Agrobacterium strains, notably *A. tumefaciens* and *A. rhizogenes*, and also by various genetically engineered transformation plasmids which include portions of the T-DNA of the tumor-inducing plasmids of Agrobacteria. The T-DNA borders can be incorporated into other transformation constructs, to facilitate integration of a stabilized exogenous gene lying between the T-DNA border elements. Other means for effecting entry of DNA into cells include viral vectors and agroinfection.

DNA constructs suitable for transformation include at a minimum the exogenous gene (promoter and coding sequence) to be transferred, flanked by at least one stabilizing DNA segment, but can involve other elements as well. The stabilized exogenous gene can be inserted into a vector, flanked by T-DNA borders, combined with a marker gene, all according to techniques known in the art. The choice of construct will be influenced by the method of transformation adopted. For example, if a ballistic transformation is desired, use of a vector may be superfluous, while flanking T-DNA borders (in addition to the stabilizing DNA segments) may be desired as a means of promoting genomic integration of the transgene.

Examples of vectors suitable for plant transformation include, but are not limited to:pCGN1547, pART27, pOCA18, pCV001, pCV002, MON200, pGV3850, pGV260, pGPTV vectors, and Mini-Ti plasmids.

References describing the foregoing and other vectors suitable for use in the invention are also included: (Mini-Ti) Framond de, A. J. (May 1983) Bio/Technology, pp. 262–269; (pCV001/pCV002) Koncz, C. and Schell, J. (1986) Mol. Gen. genet. 204:383–396; Klee, H. J. et al. (1985) Bio/Technology 3:637–642; (pCGN1547) McBride, K. E. and Summerfelt, K. R. (1990) Plant Mol. Biol. 14:269–276; Hoekema, A. et al. (1985) Plant Mol. Biol. 5:85–89; (pGV3850) Zambryski, P. et al. (1983) EMBO J. 2:2143–2150; (pOCA18) Olszewski, N. E. et al. (1988) Nucl. Acids Res. 16(22):10765–10782; (pART 27) Gleave, A. P. (1992) Plant Mol. Biol. 20:1203–1207; (pGV260) Deblaere, R. et al. (1985) Nucl. Acids Res. 13:4777; (pGPTV vectors) Becker, D. et al. (1992) Plant Mol. Biol. 0:1195–1197; (pGA vectors) An, G. et al. (1985) EMBO J. 4(2):277–284; (Binary vectors in general and cointegrate vectors in general in Chapters A2 and A3) Plant Mol. Biol. Manual, Gelvin and Schilperoot, Eds., Kluwer Academic Publishers (1988).

Virtually all plants of agronomic or horticultural value are known to be both transformable and regenerable. The techniques vary in individual detail from species to species, as is understood by those skilled in the art. The nature of applicable transformation methods to be used for a given plant species may be affected by the type of regeneration protocol that can be used in any given instance. For example, where regeneration cannot be obtained from protoplasts, the method of transformation must be suitable for whole cells or tissues. Where the plant species is difficult to transform using Agrobacterium, the alternative of ballistic transformation may be preferred. All such considerations are matters well-known to those of skill in the art.

Examples of plants suitable for use in the invention include, but are not limited to, those plants that are members of Solanaceae, Apocynaceae, Chenodiaceae, Polygonaceae, Boraginaceae, Compositae, Rubiaceae, Scrophulariaceae, Caprifoliaceae, Leguminosae, Araccae, Moraceae, Euphorbiaceae, Brassicaceae, Primulaceae, Violaceae, Protulaceae and Rosaceae. In addition, plants of the following families are suitable for use in the invention: polypodiaceae, umbelliferae, liliaccae, crucifereae, gramineae, geranaceae, ranunculceae, begoniaceae, labiatae, caryophyllaceae, balsaminaceae, papilionaceae, gesneriaceae, violaceae, araliaceae, as well as plants commonly known as: fern, carrots, leek, asplenium, radishes, celery, onions, fennel, wheat, rye, barley, corn (maize), soybean, oats, rices, geraniums, violets, windflowers, ornamental asparagus, begonias, flame nettle, lark spur, carnations, gilliflowers, Busy Lizzy, lupin, crowflower, sage, bell flowers, soap herbs and Panax ginseng. Specific mention is also made of the following plants: tomato, melon, watermelon, pepper, lettuce, beans, brassica including rapeseed plants, cabbages, broccolis, cauliflowers, sunflowers, sugar beet, violas, begonia, pelargonium peltatum, pelargonium hortorum, corn (maize), sweet corn, Cyclamen and Impatiens.

EXAMPLES

Example 1

Isolation of Maize Repetitive Sequences (MRS)

Figure 1A:
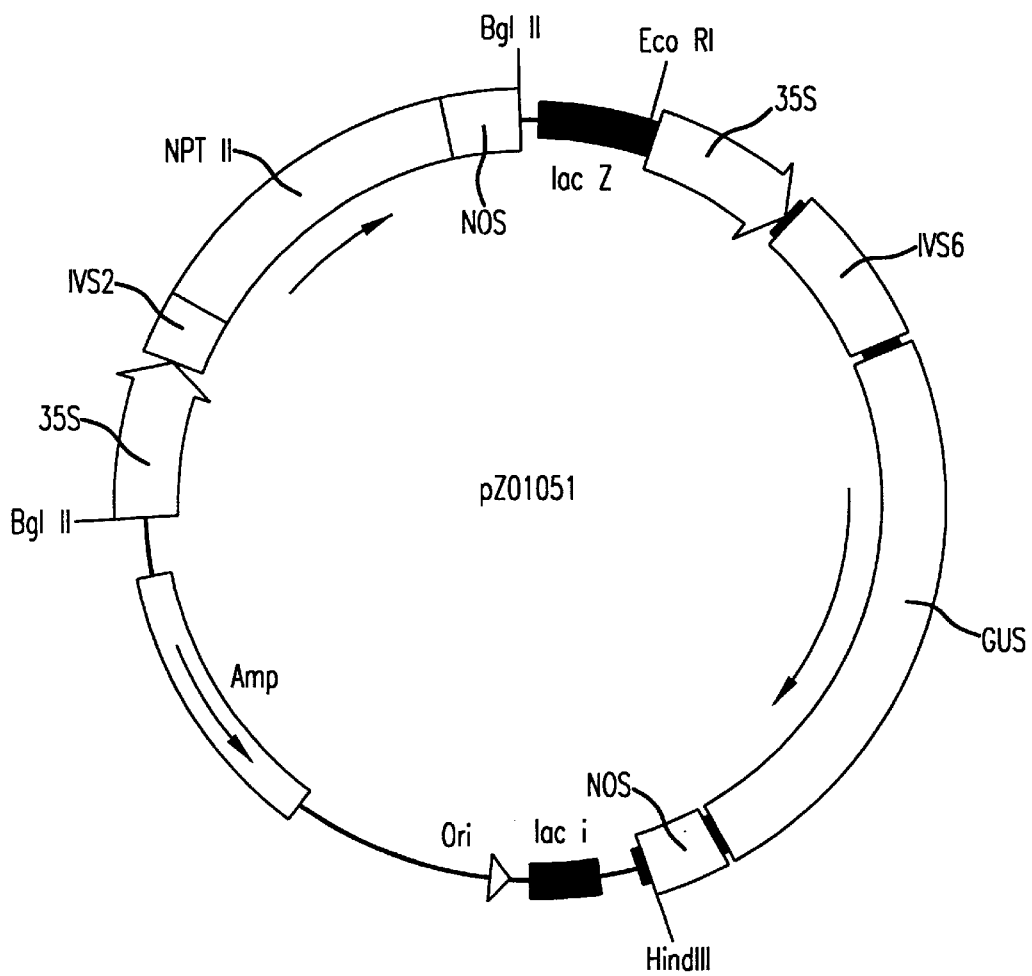
FIG. 1a is a diagram of the plasmid pZO 1051, as described in Example 2.
Figure 1B:
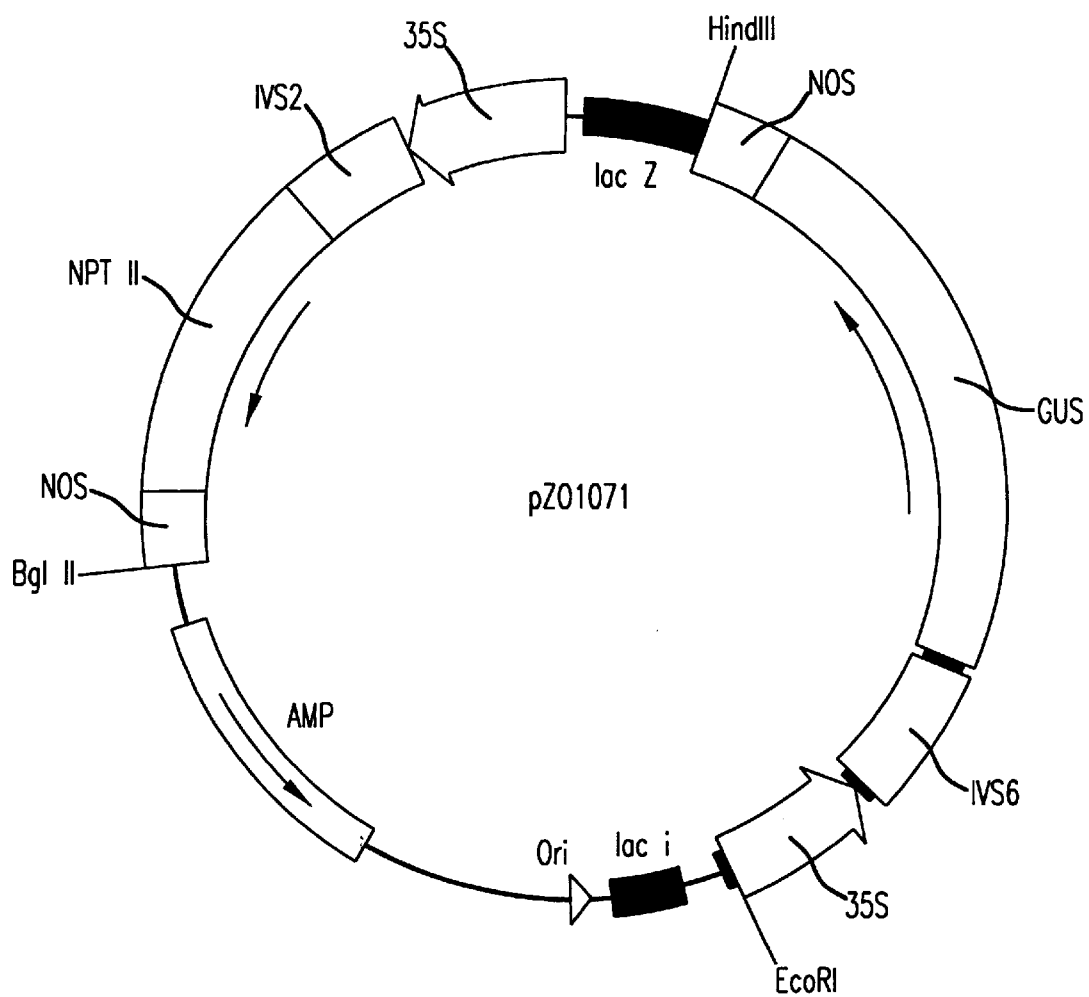
FIG. 1b is a diagram of the plasmid p20 1071, as described in Example 2.

A library of *Zea mays* L. (A3780) genomic DNA is constructed in pTZ19R (Pharmacia) by restricting genomic DNA with EcoRI plus HindIII, separating the resulting fragments on 0.6% low-melting point agarose, excising the region containing fragments from 1 to 3 kb in size, diluting, melting and ligating to EcoRI plus HindIII cut pTZ19R, and transforming in *E. coli* C600 cells. Unless otherwise specified, methods for cloning and preparing plasmid DNA are essentially as described (Maniatis et al. (1982) Molecular Clonin , Cold Spring Harbor Laboratory). In general, all cloning is done with DNA fragments excised from low-melt agarose. Individual colonies from this library are grown in individual wells of microtiter dishes. To screen this library for repetitive sequences, cells from each well are transferred to nitrocellulose filters using a dot-blot apparatus, lysed thereon using dilute NaOH, washed, then the filters are dried and baked. The filters are hybridized to maize genomic DNA labelled by nick translation. Only colonies corresponding to cloned repetitive DNA give a strong signal under these conditions. About twenty clones are further analyzed by DNA preparation, restriction site mapping, and southern blotting. Six are selected for further testing and their inserts are named MRS1, MRS2, MRS3, MRS4, MRS5, and MRS6. The maize inserts are cut at their HindIII sites, made blunt by treatment with T4 DNA polymerase, then EcoRI linkers are ligated using T4 DNA ligase. Excess linkers are removed by treatment with EcoRI, which also frees each fragment from the plasmid vector. Each fragment is excised from low-melt agarose and ligated to pZO1071 (Example 2), which has been cut with EcoRI and treated with calf intestinal alkaline phosphatase (CAP) and excised from low-melt agarose (see FIG. 1). In general, only one orientation of each insert in pZO1071 is recovered. For cloning into EcoRI cut plus CAP treated pZO1051, each fragment is excised from its corresponding insert in pZO1071 by restriction with EcoRI. In this case, the effort is made to recover inserts in each of the two possible orientations (designated "a" and "b") for MRS3, 4, and 5. The sequence of MRS5 is given in Table 1A (SEQ ID NO:1). Table 1B gives the sequence of MRS4 (SEQ ID NO:2) and Table 1C gives a partial sequence of MRS3 (SEQ ID NO:3).

TABLE 1A

MRS 5
Eco RI

GAATTCTTATCGATACTGGAACTCAGAGCATAGGGGGAAAGTCGATTTATGGATGGAATCAAATACGCA
                   A Box(9/10)Topo II(12/15)

GTATTTACAGAAAAGAGTCTTCGTTTATTGGGAAAGAATCAATATACTTTTAATGTCGAATCGGGATTCA

CTAAGACAGAAATAAAGCATTGGGTCGAACTCTTCTTTGGTGTTAAGGTAGTAGCTGTGAATAGCCATCG

ACTACCCGGAAAGGGTAGAAGAATGGGACCTATTCTGGGACATACAATGCATTACAGACGTATGATCATT
                   T Box(9/10)

ACCCTTCAACCGGGTTATTCTATTCCACTTCTAGATAGAGAACGAACTAAAGGAGAATACTTAATAATAC
       Topo II(13/15)

GGCGAAACATTTATACAAAACACCTATCCCGAGCACACGCAAGGGAACCGTAGACAGGCAAGTGAAATCC

AATCCACGAAATAAATTGATCCATGGACGGCACCGTTGTGGTAAAGGTCGTAATGCCAGAGGAATCATTA

CCGCAAGGCATAGAGGGGGAGGTCATAAGCGCCTATACCGTAAAATCGATTTTCGACGGAATCAAAAAGA

CATATCTGGTAGAATCATAACCATAGAATACGACCCTAATCGAAATGCATACATTTGTCTCATACACTAT
                   T Box(8/10)

GGGGATGGTGAGAAGAAGATATATTTTACATCCCAGAGGGGCTATAATTGGAGATACTATTGTTTCTGGTA
                                                                    Sna BI

CAAAAGTTCCTATATCAATGGGAAATGCCCTACCTTTGAGTGCGGTTTGAACTATTGATTTACGTAATTG

TABLE 1A-continued

```
GAAGTAACCAATTAGGTTTACGACGAAACCTAGAAATCGATCACTGATCCAATTTGACTACCTCTACGGG

ATAGACCTCAACAGAAAACTGTTGAGTAACGGCAGCAAGTGATTGAGTTCAGTAGTTCCTCATAGAAAAT

TATTGACTCTAGAGATATGGTAATATGGAGAAGACAAAATTGTTTGAAGCACGCACAGAACCGGAAGCGC

CCCTTGTTTCAAAGAGAGGAGGACGGGTTATTCACATTTAATTTGATGGTCAGAGGCGAATTGAAAGTTA

AGCAGTGGTAATTAAGACCCCCGGGTGAAAATAGGGATGTCTCCTACGTTACCCATAATATGTGGAAGTA

TCGACGTAATTTCATAGAGTCATTCGATCTGAATGCTACATGAAGAACATAAGCCAGATGACGGAACGCG

GAGACCTAGGATGTAGAAGATCATAACATGAGCGATTCGGCGGATTTGGATTCCTTTTCTATATATCCAC

TCATGTGGTACTTCATCATACGATTCATATAAGATCCATCTGTCTAGAGATCGTCATATACATCTAGAAA

GCCGTATGCTTTGGAAGAAGCTT
                  HIND III

60% AT
```

TABLE 1B

```
gaattctgtggaaagccgtattcgatgAAAGTCGTATGTACGGCTTGGAGGGAGATCTTTCCTATCTTTC

GAGATCCaccctacaatatgGGGCCAAAAAGCCAAAAAAATAAGTGATTCGTTTTTAGCCCTTATAAAAA

GAAAACGGATTCTTGAACCTCTTTCACGCTCATGTCACGTCGAGGTACTGCAGAAAAAAGAACCGCAAAA

TCCGATCCAATTTTTCGTAATCGATTAGTTAACATGGTGGTTAACCGTATTATGAAAGACGGAAAAAAAT

CATTGGCTTATCAAATTCTCTATCGAGCCGTGAAAAAGATTCAACAAAAGACAGAAACAAATCCACTATT

GGTTTTACGTCAAGCAATACGTAGAGTAACTCCCAATATAGGAGTAAAAACAAGACGTAATAAAAAAGGA

TCGACGCGGAAAGTTCCGATTGAAATAGGATCTAAACAAGGAAGAGCACTTGCCATTCGTTGGTTATTAG

AAGCATCCCAAAAGCGTCCGGGTCGAAATATGGCTTTCAAATTAAGTTCCGAATTAGTAGATGCTGCCAA

AGGGAGTGGGGGTGCCATACGCAAAAAGGAAGCGACTCATAGAATGGCAGAGGCAAATAGAGCTCTTGCA

CATTTTCGTTAATCCATGAACAGAATCTAGGTATGTAGACACATGGATCCATACATCTCGATCGGAAAAG

AATCAATAGAAGGAGAATCGGACGATATCTTTTTCGAAACAAATAAAAAGGAAAAAAAAGAGAAAACAGA

AATCATGATCAACTAAGCCTCTCGGGGGCTTGCTTAAGAATAAGAAAGAGGAATCTTATGGAAATAGCAT

GGAATAAGGTTTGATCCTATTCATGGGGATTCCGTAAATATCCCATTCCAAAAATCGAAACAATCGGGAC

TTTTCGGAGATTGGCTGCAGTTACTAATTCATGATCTGGCATGTACAGAATGAAAACTTCATTCTCGATT

CTACGaGAATTTTTATGAAAGCGTTTCATTTGCTTCTCTTCCATGGAAGTTTCATTTTCCCAGAATGTAT

CCTAATTTTTGGCCTAATTCTTCTTCTGATGATCGATTTAACCTCTGATCAAAAAGATAGACCTTGGTTC

TATTTCATCTCTTCAACAAGTTTAGTAATAAGCATAACGGCCCTATTGTTCCGATGGAGAGAAGAACCTA

TAATTAGCTTTTCGGGAAATTTCCAAACGAACAATTTCAACGAAATCTTTCAATTTCTTATTTTATTATG

TTCAACTTTATGTATTCCTCTATCCGTAGAGTACATTGAATGTACAGAAATGGCTATAACAGAGTTTCTG

TTATTCGTATTAACAGCTACTCTAGGGGAATGTTTTTATGTGGTGCTAACGATTTAATAACTATCTTTG

TAGCTCCAGAATGTTTCAGTTTATGTTCCTACCTATTGTCTGGATATACCAAGAGAGATCTACGGTCTAA

TGAGGCTACTATGAAATATTTACTCATGGGTGGGGCAAGCTCTTCTATTCTGGTTCATGGTTTCTCTTGG

CTATATGGTTCATCTGGGGGGGAGATCGAGCTTCAAGAAATTGTGAATGGTCTTATCAATACACAAATGT

ATAACTCCCCAGGAATTTCAATTGCGCTTATATTCATCACTGTAGGACTTGGGTTCAAGCTTU
```

TABLE 1C

```
AAGCTTCTTCCAAAGCATACGGCTTTCTAGATGTATATGACGATCTCTAGACAGATGGATCTTATATGAA

TCGTATGATGAAGTACCACATGAGTGGATATATAGAAAAGGAATCCAAATCCGCCGAATCGCTCATGTTA

TGATCTTCTACATCCTAGGTCTCCGCGTTCCGTCATCTGGCTTATGTTCTTCATGTAGCATTCAGATCGA

ATGACTCTATGAAATTACGTCGATACTTCCACATATTATGGGTAACGTAGGAGACATCCCTATTTTCACC

CGGGGGTCTTAATTACCACTGCTTAACTTTCAATTCGCCTCTGACCATCAAATTAAATGTGAATAACCCG

TCCTCCTCTCTTTGAAACAAGGGGCGCTTCCGGTTCTGTGCGTGCTTCAAACAATTTTGTCTTCTCCATA

TTACCATATCTCTAGAGTCAATAATTTTCTATGAGGAACTACTGAACTCAATCACTTGCTGCCGTTACTC

AACAGTTTTCTGTTGAGGTCTATCCCGTAGAGGTAGTCAAATTGGATCAGTGATCGATTTCTAGGTTTCG

TCGTAAACCTAATTGGTTACTTCCAATTACGTAAATCAATAGTTCAAACCGCACTCAAAGGTAGGGCATT

TCCCATTGATATAGGAACTTTTGTACCAGAAACAATAGTATCTCCAATTATAGCCCCTCTGGGATGTAAA

ATATATCTCTTCTCACCATCCCCATAGTGTATGAGACAAATGTATGCATTTCGATTAGGGTCGTATTCTA

TGGTTATGATTCTACCAGATATGTCTTTTTGATTCCGTCGAAAATCGATTTTACGGTATAGGCGCTTATG

ACCTCCCCCTCTATGCCTTGCGGTAATGATTCCTCTGGCATTACGACCTTTACCACAACGGTGCCGTCCA

TGGATCAATTTATTTCGTGGATTGGATTTCACTTGCCTGTCTACGGTTCCCTTGCGTGTGCTCGGGATAG

GTGTTTTGTATAAATGTTTCGCCGTATTATTAAGTATTCTCCTTTAGTTCGTTCTCTATCTAGAAGTGGA

ATAGAATAACCCGGTTGAAGGGTAATGATCATACGTCTGTAATGCATTGTATGTCCCAGAATAGGTCCCA

TTCTTCTACCCTTTCCGGGTAGTCGATGGCTATTCACAGCTACTACCTTAACACCAAAGAAGAGTTCGAC

CCAATGCTTTATTTCTGTCTTAGTGAATCCCGATTCGACATTAAAAGTATATTGATTCTTTCCCAATAAA

CGAAGACTCTTTTCTGTAAATACTGCGTATTTGATTCCATCCATAAATCGACTTTCCCCCCTATGCTCTG

AGTTCCAGTATCGATAAGAATTC
```

Example 2

Construction of pZO1051 and pZO1071

The EcoO 1091 site of pUC19 (Yanisch-Perron, C. et at. (1985) Gene 33:103–119) is converted to a BgIII site by filling in and ligation of a BgIII linker to give pZO919. The NPT II gene cassette is assembled by treating pZO919 with BgIII and CAP and ligating to it a 1.7 kb BgIII to SmaI fragment, consisting of the 35S promoter (AluI to DdeI, Franck A. et al. (1980) Cell 21:285–294), maize Adh1S intron 2 (Freeling, M. and Bennett, D. C. (1985) Ann. Rev. Genet. 19:297–323), TN-5 neomycin phosphotransferase gene (Beck, E. et al. (1982) Gene 19:327–336), and a 0.24 kb blunt to BgIII fragment consisting of the NOS terminator (Bevan, M. et al. (1983) Nucl. Acids Res. 11:369–385). Plasmid pZO921 consists of the particular orientation of this cassette in pZO919 in which the NOS terminator is closest to the EcoRI site of the multiple cloning site. The β-glucuronidase (GUS) cassette consists of the 35S promoter DdeI to DdeI, Franck et al. ibid), maize Adh1S intron 6 (Freeting and Bennett, ibid.), GUS gene (Jefferson, R. A. et al. (1986) Proc. Natl. Acad. Sci. 83:8447–8451), and NOS terminator. The GUS cassette is then inserted as a 3.1 kb EcoRI to HindIII fragment into EcoRI plus HindIII cut pZO921 to construct pZO1051 (see FIG. 1).

The orientation of the multiple cloning site of pZO919 is reversed by replacing its PvuII fragment with the corresponding PvuII fragment (ca. 300 bp) from pUC18 to form pZO930. The GUS cassette is then inserted again as an EcoRI to HindIII fragment to form pZO1068. Finally, the NPT II cassette from pZO921 is cloned as a 1.9 kb BamHI to BgIHI piece into the BgIII site of pZO1068. The orientation of the NPT II cassette for which the 35S promoter is closest to the HindIII site is named pZO1071 (see FIG. 1).

Example 3

Transient Assays

Preparation and electroporation of protoplasts of maize black mexican sweet (BMS) suspension cells and tobacco suspension cells is done essentially as described (Fromm et al. (1985) Proc. Natl. Acad. Sci. USA 82:5824–5828). Electroporated protoplasts are cultured in the dark for one to two days, then β-glucuronidase assays are done essentially as described (Jefferson, R. A. (1987) Plant Mol. Biol. Rep. 1:387–405).

Table 2 shows the results of a transient assay in electroporated BMS protoplasts. The GUS activity of pZO1071 is set to 1.00. Results are given for each MRS cloned into the EcoRI site of either pZO1051 or pZO1071. When electroporated into BMS protoplasts, pZO1051 has only about 20% as much GUS activity as pZO1071. (Conversely, when NPT II activity is measured, pZO1071 has somewhat less activity than pZO1051, data not shown.) Thus the gene which is downstream in the direction of transcription shows reduced expression. The upstream gene has activity unchanged from that found when another cassette is not present on the same plasmid. Each MRS is tested for its ability to relieve the inhibition. Whereas none of the MRS has a strong effect on GUS expression per se, as shown by the results when cloned into pZO1071, MRS 3, 4 and 5 each show some ability to restore the activity of the GUS cassette of pZO1051 to its full level.

TABLE 2

RELATIVE GUS ACTIVITY IN BMS PROTOPLASTS

| INSERT | SIZE | 1071 | 1051 |
|---|---|---|---|
| NONE |  | 1.00 | 0.18 |
| MRS1 | 1.5 | 1.2 | 0.25 |
| MRS2 | 1.2 | 1.9 | 0.17 |
| MRS3 | 1.5 | 2.1 | 0.72 |
| MRS4 | 1.7 | 2.2 | 0.66 |
| MRS5 | 1.4 | 2.4 | 0.99 |
| MRS6 | 1.8 | 1.9 | 0.12 |

Example 4

In a further experiment, results from electroporating plasmids into tobacco protoplasts are obtained. The effect of the orientation of the MRS relative to the GUS cassette is also examined. Table 3 shows that the GUS activity from pZO1051 is also much reduced compared to pZO1071 in tobacco protoplasts, that MRS3, MRS4, and MRS5 can relieve this inhibition, and that there may be a modest preference for orientation of MRS4 and MRS3. In MRS3, the (a) orientation occurs when the original EcoRI site is proximal to the promoter. In MRS4, the (a) orientation occurs when the original HindIII site is proximal to the promoter. In MRS5, the (a) orientation occurs when the original HindIII site is proximal to the promoter.

TABLE 3

RELATIVE GUS ACTIVITY IN TOBACCO PROTOPLASTS

| PLASMID | INSERT IN pZO1051(OR) | RELATIVE GUS(SE) |
|---|---|---|
| 1071 |  | 1.00(.26) |
| 1051 |  | 0.40(.05) |
| 1442 | MRS3 (a) | 1.12(.12) |
| 1466 | MRS3 (b) | 0.88(.12) |
| 1443 | MRS4 (a) | 1.00(.11) |
| 1463 | MRS4 (b) | 1.50(.20) |
| 1464 | MRS5 (a) | 0.83(.09) |
| 1465 | MRS5 (b) | 0.84(.13) |

Example 5

Activity of Subclones of MRS5

To discover whether there is a region within the MRS which retains the ability to insulate the GUS gene in pZO1051, the ends of the three fragments of MRS 5, as described in the restriction map below Table 4, are converted to EcoRI sites to allow cloning of these fragments into the EcoRI site of pZO1051. Each orientation is recovered for each fragment. The orientations correspond to those of pZO1464 and pZO1465. The results of transient assays in BMS and in tobacco protoplasts shown in Table 4 clearly indicate, at least in the case of MRS5, that each fragment retains only a portion of the insulating ability. The A orientation is the same as described in Example 4 for MRS5(a).

TABLE 4

ACTIVITY OF FRAGMENTS OF MRS5

| PLASMID | INSERT | RELATIVE GUD | |
|---|---|---|---|
|  |  | BMS | TOBACCO |
| 1071 |  | 1.0 | 1.0 |
| 1051 |  | 0.20 | 0.40 |
| 1464 | MRS5-A | 1.0 | 1.12 |
| 1465 | -B |  | 0.88 |
| 1455 | HIND III-SNA BI, 0.60-A | 0.50 | 0.56 |
| 1454 | -B | 0.34 | 0.64 |
| 1468 | XBA I-XBA I, 0.59-A | 0.54 | 0.73 |
| 1469 | -B | 0.31 | 0.49 |
| 1456 | SNA BI-ECO RI, 0.75-A | 0.65 | 0.81 |
| 1457 | -B | 0.26 | 0.80 |

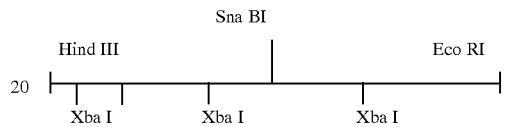

Example 6

Results in Stable Callus Cultures

Plasmids pZO1071, pZO1051, pZO1442, pZO1443, and pZO1464 are electroporated into BMS protoplasts, which are plated on filters, then cultured on suitable agar containing medium with a layer of feeder cells and kanamycin, 75 mg/L. Extracts are prepared from about twenty kanamycin resistant calli for each construct. To determine that each callus is a true transformant, NPT II activity is confirmed by ELISA (5 Prime, 3 Prime, Inc.). GUS activity is measured spectrophotometrically and normalized to total protein.

The frequency of GUS-expressing calli is thought to be highest for those constructs containing MRS3, 4 or 5, and the levels of GUS activity found are more uniform as well.

GUS-expressing calli are maintained for several months on kanamycin containing medium and periodically assayed for GUS activity. Individual calli transformed with pZO1051 or pZO1071 are found to have lost GUS expression, and the fraction of such calli is found to increase over several months. however, transformants of [one or more of] pZO1442, pZO1443, and pZO1464 are found to maintain GUS expression at a significantly higher frequency.

Thus these MRS which were originally identified to have "boundary" properties in transient assays are found to also behave as stabilizing DNA segments in stable transformants.

Example 7

Stability of Progeny

A similar experiment to that of Example 6 is performed, except that a regenerable maize cell line is transformed, either via electroporation or the ballistic method, depending on the cell line. Stable calli recovered after growth on selective media are transferred to suitable regeneration medium for shoot initiation, the shoots are moved to rooting medium, finally resulting in plants which are grown to maturity, characterized for GUS and NPT II expression, and out-crossed or selfed. The resulting first progeny generation is also characterized for transgene expression. The expression and heritability of the transgenes continue to be followed for succeeding generations.

What is found is that those families of transformants originated from plasmids containing certain MRS show improved stability of expression of the GUS gene, particularly over the generations, when compared to families originating from pZO1051 or pZO1071.

Example 8

Sequencing, Cloning and Transient Assays of Matrix Associated Regions (MARS)

Two fragments, MAR1 (maize 0.8 kb AT rich region) and MAR2 (maize 1.25 kb region with ARS3), found within a 5 kb maize EcoR1 fragment originally cloned by R. Berlani et al. (1988 Plant Mol. Biol. 11:161–172) have nuclear matrix binding activity. The sequence of the MAR1 fragment is given in Table 5A (SEQ ID NO:4) and that portion of MAR2 not previoulsy sequenced is given in Table 5B (SEQ ID NO:5) along with the published portion of MAR2 named ARS3 (Berlani et al. 1988 Plant Molecular Biology 11:173–182). Additionally the sequence from the $SAR_L$ a region from a soybean small heat shock gene (MAR3) (soybean HSP17.6 0.4 kb SARL) is shown in Table SC (SEQ ID NO:6). (Schöffl et al. Transgenic Res. 2 93–100 (1993)). The fragments are sequenced by standard dideoxy methods.

Standard cloning procedures are used in the construction of plasmids for gene activity. MAR1 is subcloned from pZMA321 as an EcoR1-HindIII fragment into pT7T3-18U (Pharmacia) to form pZO1927. MAR2 is subcloned from pZMA321 as a HindIII fragment into pT7T3-18U to form PZO1929. The HpaII end of MAR3, originally a HpaII-EcoRI fragment, had already been converted to EcoRI in pSVB20-$SAR_L$ (Schöffl, supra). For cloning into EcoRI sites, pZO1927 was cut with HindIII, treated with T4 DNA polymerase I, then EcoRI linkers (NEB) added by ligation, followed by restriction with EcoRI. The HindIII ends of MAR2 are converted to EcoRI sites by PCR with pZO1029 as template using the primers "1929ECOR" TGAGGAATCGCGGTCTATCCCCCGCACG, SEQ ID NO: 7, for the M13R side, and "1929ECOU", GTCGGMAATTCAAGTCCACAACTGAGACAAG, SEQ ID NO: 8, for the M13U side, followed by restriction with EcoRI. MAR3 is directly cloned into EcoRI sites following restriction with EcoRI. For cloning into HindIII sites, pZO1927 and pSVB20-SARL are cut with EcoRI, treated with T4 DNA polymerase I, HindIII linkers ligated, followed by restriction with HindIII. MAR2 is cloned directly into HindIII sites following restriction with HindIII.

Plasmids pZO1071 and pZO1051 are constructed according to Example 2 and each MAR fragment is cloned into the EcoR1 sites. These plasmids are contructed according to Example 2. For one orientation of each MAR at EcoRI, a second copy is also cloned into the HindIII site to give plasmids in which the GUS cassette is bound by a pair of MARs.

Preparation and electroporation of protoplasts of maize black mexican sweet (BMS) suspension cells are decribed in Example 3. Table 6 shows the mean results of a number of transient assays in electroporated BMS protoplasts. The GUS activity of pZO1071 is set to 1.00. Results are given for each MAR cloned into the EcoRI site of either pZO1071 or pZO1051. For MAR1 the A orientation occurs when the ClaI site is proximal to the promoter. For MAR2, the A orientation occurs when the pair of Sac II sites are proximal to the promoter. For MAR3 the A orientation occurs when the EcoRV site is distal to the promoter. Results with pZO1701 indicate that MARS do not significantly effect expression in the GUS cassette in either the 5'(EcoRI) or 3'(HindIII) locations. GUS activity from pZO1051 is also reduced compared to pZO1071. Each MAR tested can partially relieve this inhibition.

TABLE 5A

Sequence of MAR1(pZO1927)

Eco RI                                                              A Box (8/10)
GAATTCAGGTAATCCCGTCGGCCCAAAACCGACGGGAATTAATAGTCGGAGTTTAGTTAATTCTCGTAGG

Topo II (13/15)
TAGCTGATGGGAATTAGTAATTCCCGTCGGTTTACGCGCAGTCGACATGAATTAATTAGTCAATTCCCGT

CAACCAGTTAATTTCTGTCGGACACGTCTGACCCATGGGAATTATTCGACGAGGTAATCCAAATCCACGA

Topo II (13/15)
GGTCTTTGTAACAATTAATAGAGAATGCAAACTTGGACTTGATTGACATCAGCTGGGTCACGAAATCGAG

AACGGTCACATCAGTGTGCTCATGAAGAGGCTCTTTTGACGCTTTGAGGAGGTCAAAGAACTTCTGAACC

TCCCGGTGTAGTGAATCATGATGATATGGGGCCAATTTCGACTGCAAATCCACAAGCATCCGCCTAATAT

ARS (10/12) /T Box (9/10)
TATATATTTGTGACAAAGCAATTGCATGGTTTAGAAACATCTGAGTTTTGGCAAACCATTCACTTGTGTG

ACACCCACCCTTTTTGAAACCTTCATACATCCAATCACGTCTATCACCCATTATTGCGGCTGTGTACAAG

TABLE 5A-continued

Sequence of MAR1(pZ01927)

```
                AT Box
TAAGAAGTGTGTGTGAGACATTCATATTTCCTACACATCACACATAACATGTATGGTACATACATGTGAT

T Box (8/10)
GCATAGCGGTCTGAAATGAGTGACACATAGTTTGCAAAACTATATATGTAGTTGTGAAAGGGAAATAGTC

ClaI
TCAACATTTCCTATAATCGATTTGGGTGTTTGACGACCATAACAAACCTTGTGGACTAACCAGTTTGTCT

T Box (8/10)
AGTTGATCATTCCACAGGTGCATAAGTTCATCTACAACTATTCTAAATCGACTATCCAGAATACCGTAGA

HindIII
TTATTTCGGACAGGAGAAGCTT

59% AT
```

TABLE 5B

Sequence of MAR2 (pZ01929)

```
HindIII                                      Topo II(13/15)
AAGCTTCCAATCTCTCCAAGTTCCACAACTGAGACAAGTGATCATTAGTGATTATAGACTTGAGAGAGAG

AGAGAGTGATCCGTGTATTATTTATCGCTCTTGTTGCTTGGCTTTTGCAATCGTGCTTTCTTCTATTCCC

ATTCTTATTCTCAAGTGACTTGTAATCAAAGAAAGAGACACCAAGTGTGGGGTGGTCCTTGTGGGGTCTA

→
AGTGACCCGGTTGATTAAGGAGAAAGCTCAGTCGGTCTAGGTGGCCGTTTGAGAGAGGGAAAGGGTTGAA

AGAGACCCGGTCTTTGTGACCACCTCAACGGGGACTAGGTTCTTTGGAACCGAACCTCGGTAAAACAAAT

T Box(8/10)/A Box(9/10)                    T Box(8/10)
CACCGTGTCATCCGCTTTATTTCTTGGTTGATTTGTTTTCGCCCTCTCTCCTAGACTTGGATTTTATTCT

AACGCTAACCCCGGCTTGAAGTGTGCTTAAAGTTTGTAAATTTCAGTTTCCGCCTATCCACCCCCCTCTA

Topo II(13/15)
GGCGACTTTCAAGTTGCAACAATGAGGTAGTAGAATCAATACTTANATAACATGACATTAATCANTTAAC Topo II(14/15)                                         Toppo II(13/15)
AATATTCANAACGAATTAATAATTTGCAACAATTACTAGGTGTATAACAACACAGTCACCATCAAAATTC AT Box TopoII(13/15)/ARS(12/15)/T Box(9/10)
ATCAACTAATAACATCAAGCCACATAGTTTATATTTGCAACATAAATATAAAAATAGCAACTACAATGTA A Box (9/10)           Topo II(14/15)
TAAAGTCATATTAAgaCTAATAACACTATCAATTaACAAATTTAAGATAACTATAATTGCATAAAAGTTA T Box(8/10) Topo II(13/15)
ACTCTCGTCGGTCACAAAAAACTGACGAAAATAAATGTCTTAATATATATATTAAGCACCTCTAATTAAT

CACACTTTCATTTGTATCGCATAGGTCTAGGATTATACCTCGACGACTCGAATGACGTTGTCCCGTGGAG

←
GAGCTTGTGTAGGCCGGATGGCAGCACAGACGGTGGTCGTTGGAGGAGATTGCGAGGGCCGATGGGGGGG

SacII
CGTGGTGGCCGCGGTAGTGGGCAGTCCCAACAATGTGGCAGTCACGGTTGGCGCCGGCGATGGGCGTACC

SacII
GCGGTGGGCAGTCCCGACGGCGTGGCAGTGNCGGTGGGCGCCGGCGACAGGCGGACCTCCAATGGCGGAC

GACGTTGGGGCGGCCAGGCGGAGGGCGGTGGCAGTGGGCGTAGGGCGACGACGGGGACAGACCGGACCG

GCGACGACGACGTTGAAGAAAATGTTGCGGTTTGAAAATGAGCCCGTGCGGGGATAGACCGCGCCTCAT

HindIII
AAAAGCTT

54% AT
```

TABLE 5C

Sequence of MAR3 (SAR$_L$)

```
Hpa II                             ARS (11/12) A Box (9/10) ARS (10/12)
GTAACTAGCAAGTTCAGAGCATCATTTAAGTAATTAAAAGAAAAAATATTAAATATATAAATCATAAGA

Eco RV                T Box (8/10)    AT Box T Box(9/10)ARS(10/12)T Box(9/10)
TGATATCAAAAAATTCATGAACAGTCTCTTCATTTTTTTTCAATAAAAATATTTTATTTTAATTTTTA

AAATAATATCCTCATAACATTGGTTTAACTCCCAAGTTTAAAATTTACTAGTGCTAGATAAATTCTCTAA

ARS (10/12) ARS(10/12) ARS(10/12)        T Box(9/10)
GATAATGTATAGATAAAAATAAGATAAATTAGAAAATTTTTAAGGAGAGATTTTTTTTTATAAAAATTAG

AT Box ARS(10/12)T Box(9/10) Topo II (15/15)
```

TABLE 5C-continued

Sequence of MAR3 (SAR$_L$)

GTATATGTATTGGTTTTAGTTTACAGAGAAATATAATTTATATTTTCTTTTTGTGTAAATATTAATGAAA

T Box (9/10)  Eco RI
AAAATTATTCAAATTCAATCTAAATCTTAATATTTTTTTGACAGAATCC

82% at

TABLE 6

RELATIVE GUS ACTIVITY IN BMS PROTOPLASTS

| PLASMID | DESCRIPTION OF INSERT INTO pZO1071 or pZO1051 | RELATIVE GUS (SE) |
|---|---|---|
| 1071 | GUS> NPTII> | 1.00 (.08) |
| 1941 | MAR1A BUS> NPTII> | 1.12 (.08) |
| 1940 | MAR1B GUS> NPTII> | 1.10 (.10) |
| 1967 | MAR1B GUS> MAR1B NPTII> | 0.90 (.07) |
| 1970 | MAR2A GUS> NPTII> | 0.86 (0.06) |
| 1948 | MAR2B GUS> NPTII> | 1.12 (.16) |
| 1971 | MAR2B GUS> MAR2B NPTII> | 0.89 (.13) |
| 1944 | MAR3A GUS> NPTII> | 0.99 (.18) |
| 1945 | MAR3B GUS> NPTII> | 1.13 (.18) |
| 1962 | MAR3B GUS> MAR3B NPTII> | 0.98 (.04) |
| 1051 | <GUS <NPTII | 0.20 (.01) |
| 1934 | <GUS MAR1A MAR1A <NPTII | 0.90 (.06) |
| 1937 | <GUS MAR1B <NPTII | 0.65 (.06) |
| 1966 | MAR1B <GUS MAR1B <NPTII | 0.54 (.08) |
| 1942 | <GUS MAR2B <NPTII | 0.62 (.05) |
| 1968 | MAR2B <GUS MAR2B <NPTII | 0.59 (.07) |
| 1949 | <GUS MAR3 <NPTII | 0.43 (.12) |
| 1965 | MAR3B <GUS MAR3B <NPTII | 0.40 (.15) |

Example 9

Results of Stable Tansformants of MARs

A series of experiments similar to that of Example 6 are performed with MARs Incorporated into plasmids as described above. In one expermient, insertions of MAR1 in the EcoR1 site of pZO1051 are tested. The results are reported in Table 7, where (n) is the number of transformants. There is an Increase in the mean GUS levels of transformants pZO1934 and pZO1937 compared to pZO1051. The proportion of pZO1934 and pZO1937 transformants with GUS activity over 0.50 D/hr/mg protein is at least double compared to the pZO1051 transformants. Similar results are seen for contructs with two MARs bounding the GUS cassette (data not shown).

TABLE 7

STABLE GUS ACTIVITY IN BMS

| PLASMID | DESCRIPTION | Mean GUS ACTIVITY(n) (OD/hr/mg protein) | Fraction >0.5 OD/hr |
|---|---|---|---|
| 1071 | GUS> NPTII> | 0.92 (57) | 0.58 |
| 1051 | <GUS <NPTII | 0.77 (54) | 0.33 |
| 1934 | <GUS MAR1A MAR1A <NPTII | 1.26 (47) | 0.74 |
| 1937 | <GUS MAR1B <NPTII | 1.43 (46) | 0.84 |

Example 10

Isolation of the Nuclear Matrix MAR Binding System

Protoplasts are isolated from 20 grams leaves, resuspended in W5 medium, Menczel et al. (1981) Theor. Appl. Genet. 59:191–195, spun down (7' 80 g) and resuspended in 15 ml IB (20 mM hepes pH 7.4, 0.05 mM spermine, 0.125 mM spermidine, 20 mM KCI, 1% thiodiethanol, 1 M hexylene glycol, 0.5 mM EDTA, 0.5% Triton-X-100,™ 0.2 mM PMSF, 5 mg/ml aprotinin, 10 mM E64 [trans-epoxy succinyl-L-leucyclamide[4 guanidino]butane]). The protoplasts are homogenized by vortexing 20" and the resulting homogenate is centrifuged for 7' (80 g). The supernatant is centrifuged (10' 300 g) and the resulting pellet (crude nuclei) is purified on a 15% percoll gradient made in IB (15' 600 g). An interphase and/or a "smear" on the wall of the tube might appear; both fractions do contain many contaminations and few nuclei. Purified nuclei in the pellet fraction are resuspended and washing in IB buffer without Triton,™ followed by centrifugation (10' 400 g). Resulting pellet is washed and centrifuged again in the same buffer (10' 300 g); final pellet is resuspended in 2 ml IB without Triton.™ Nucleus isolation efficiency is routinely 40% as determined with DAPI staining ($12 \times 10^{6\ 5}$ nuclei).

Portions of $12 \times 10^6$ nuclei are washed in 10 ml WB (3.75 mM Tris pH 7.4, 20 mM KCI, 0.5 mM EDTA, 1% thiodiethanol, 0.05 mM Spermine, 0.125 mM Spermidine, 0.1% digitonin, tracylol 1 mg/ml) and spun down for 10' (400 g). Washed pellets are resuspended in 100 µl WB and the nuclear matrix is stabilized by incubating for 20' at 42° C. in a shaking water bath. Histone proteins are extracted by incubating the stabilized nuclei with 10 ml LIS-HLE buffer (20 mM Hepes pH 7.4, 0.1 M LiAc, 1 mM EDTA, 4 mg/ml LIS [3',5'-diiodosalicylate], 0.1% digitonin, 25 µg/ml tracylol, 1.5 mM PMSF) for 5' at room temperature. The chromosomal DNA, which is not bound to the skeleton of the nuclei (±90%), looped out; after centrifugation (3' 13.000 g) the extracted nuclei appear as a fluffy pellet, consisting of a stabilized nuclear skeleton (the nuclear matrix or nuclear halos) associated with looped out chromosomal DNA. These matrices are washed 3 times with 12 ml DB (20 mM Tris pH 7.4, 20 mM KCI, 70 mM NaCl, 10 mM MgCl$_2$, 0.05 mM Spermine, 0.125 mM Spermidine, 0.2 mM PMSF); the last matrix pellet is resuspended in 9.6 ml DB containing 1200 units restriction enzyme. Looped out DNA is removed by digestion for 60' at 37° C. At that stage the matrices are suitable for DNA binding assays to select MAR sequences.

Example 11

Characterization of Nuclear Matrix Binding Assays to Test Potential MAR DNA Sequences A nuclear matrix MAR binding system, prepared from $10^6$ nuclei, is incubated overnight in DB buffer at 37° C.

with 5 ng γ-$^{32}$P-end labelled digested plasmid carrying potential MAR sequences. Binding of MAR DNA fragments will take place either at "empty" matrix binding sites or at "occupied" matrix binding sites ("displacement" binding of endogenous MARs). After binding, the mixture is spun down; the pellet (containing the nuclear matrix MAR binding system, associated with bound labelled DNA MAR fragments) is washed once with DB and spun again. The two supernatant fractions (containing the unbound labelled DNA fragments) are pooled and the final pellet is resuspended in 200 μl DB. DNA is isolated from both the supernatant and the pellet fractions by a SDS/proteinase K treatment, followed by a phenol/chloroform extraction, two ether extractions and an ethanol precipitation. Both the DNAs isolated from the supernatant—and the pellet—fractions are electrophoresed on horizontal agarose gels, the gels are dried and autoradiographic exposure is performed for 1–3 days at –70° C. with intensifying screens. DNA fragment end-labelling, DNA extractions, electrophoresis and X-ray exposures are all performed according to Maniatis (Maniatis et al. 1989).

Figure 2:
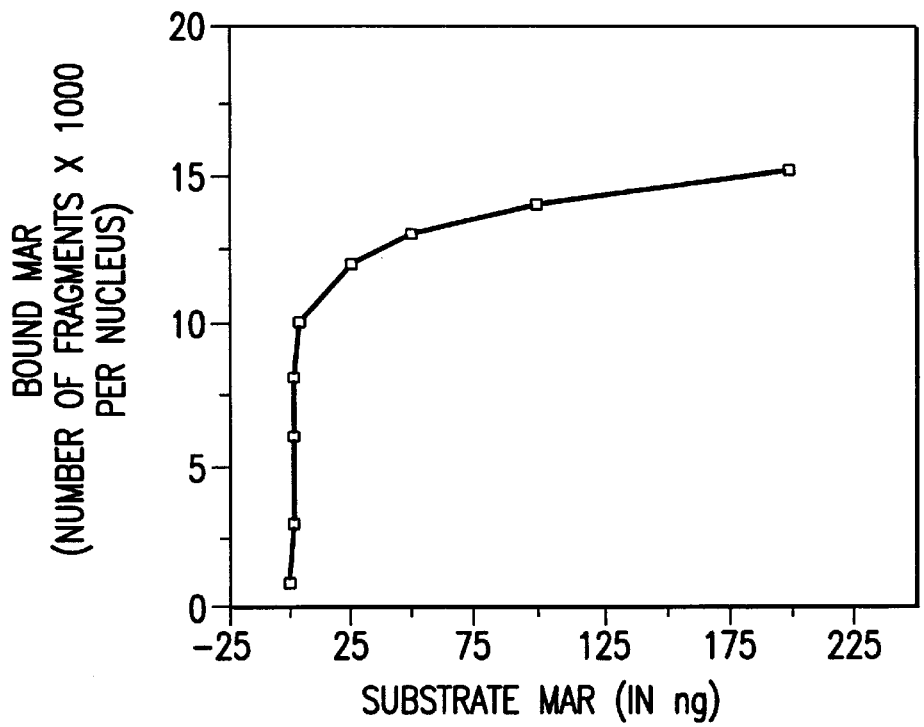
FIG. 2 is a graph showing saturation of MAR binding to nuclear matrix as the amount of MAR DNA is increased. See Example 9.
Figure 3:
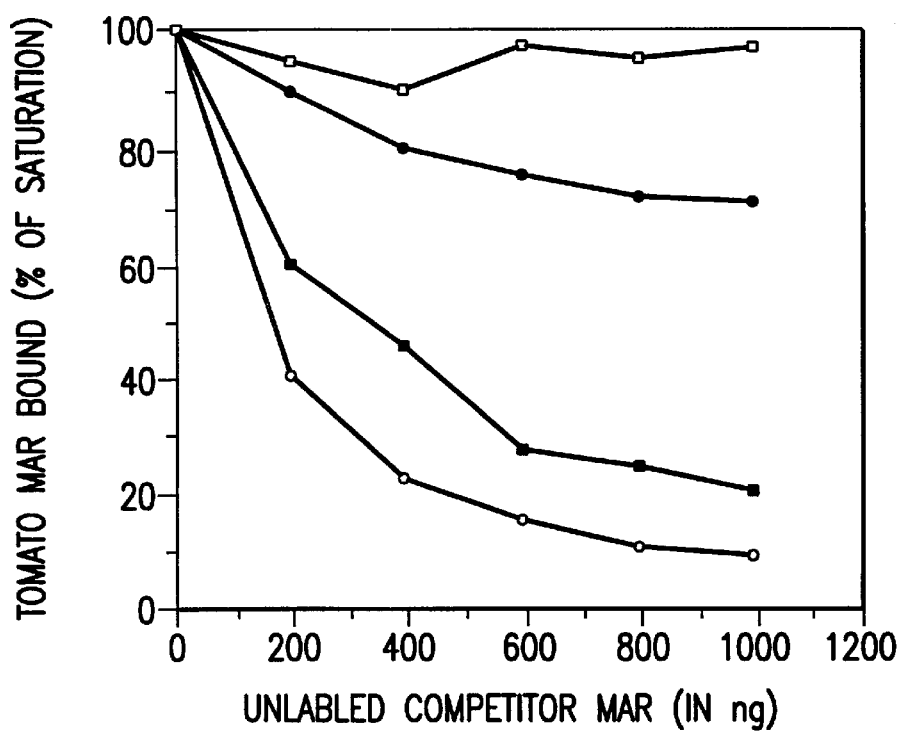
FIG. 3 is a graph showing competition of tomato MAR binding to tomato nuclear matrices as amounts of competitor MAR DNA is added.

To determine affinity of binding a series of binding experiments are performed in which the concentration of nonspecific sonicated E. coli competitor DNA is varied. Depending on the quality of the nuclear matrix MAR binding system and the affinity of the DNA fragments to be bound, different concentrations of competitor DNA are needed to result in specific binding of only the MAR fragment. FIG. 2 represents an example of such binding; without E. coli competitor DNA the MAR-containing fragments are bound to the nuclear matrix system as well as all the other vector fragments (nonspecific condition). However, whereas the vector fragments are easily displaced into the supernatant by increasing E. coli DNA concentrations, only the binding of the MAR fragment persists under stringent competition conditions (20 μg E. coli DNA is a 20,000 molar excess over the 1 kbp MAR fragment). The amount of E. Coli competitor DNA which prevents specific MAR binding, is a reference for the binding affinity of the MAR fragment.

Binding in such a system is specific as only the MAR-containing fragment is bound to the pellet fraction when the proper nonspecific E. coli competitor DNA quantity is applied. Binding in such a system Is also saturable as liquid scintillation counting of a bound tomato MAR fragment in experiments with increasing concentrations of added end-labelled restriction fragments containing that tomato MAR [1–250 ng], show that between 50 and 100 ng fragment the maximum binding level is obtained (see FIG. 2).

MAR binding sites in nuclear matrices are nonselective for a specific MAR fragment as other MAR fragments can compete for binding effectively, consequently MAR binding is also reversible. In FIG. 4 this is demonstrated for the binding of a tomato MAR; it can be competed to approximately 20% by a 6-fold excess of rat MAR. This suggests that MAR matrix interaction is conserved during evolution.

When heat stabilization during nuclear matrix isolation is omitted, the nuclear matrix skeleton (internal matrix consisting of residual nucleoli and granular clusters of electron dense clusters embedded in a highly branched network of thin filaments) is not stabilized, resulting in an "empty" nuclear shell, consisting of only the external lamina. specific and saturable MAR DNA fragment binding, similar to the nuclear matrix system, is also possible with nuclear shells. The only difference is that binding at the nuclear shell binding sites is more rapidly competed by nonspecific E. coli DNA, demonstrating that the number of MAR binding sites in nuclear shells is lower relative to the nuclear matrix.

Example 12

Isolation of Plant MAR DNA Sequences from Nuclear Matrices

Nuclear envelopes are isolated from tomato protoplasts according to Kaufmann and Shaper (1984) Exp. Cell Res. 155:477–497; Lam B1-like molecules are isolated from those envelopes as described by Aebi et al. (1986) Nature 323:560–564. Lamin B1 is coupled to inert columns, e.g., sepharose CL 4B, using cyanogen bromide, which are used as selection tools for potential MAR sequences.

Tomato nuclear chromosomal DNA is isolated according to Bernatzki, R. and Tanksley, S. (1986) Plant Mol. Biol. Reporter 4:37–41. Mbol digested tomato DNA is passed over a Lamin B1 affinity column and specifically bound DNA fragments are eluted, cloned and further characterized for nuclear matrix binding in the nuclear matrix MAR binding system as described in Example 9.

Example 13

Isolation of Plant MAR DNA Sequences from a Potential Chromatin Loop Surrounding a Stable Transgene The tomato spotted wilt virus (TSWV) (Peters, D. et al., Proceedings USDA Workshop, Beltsville, Md., Hsu and Lawson (eds.), Nat. Tech. Inf. Serv., Springfield, Va. (1991); Gielen, J. J. L. et al. (1991) Bio/Technology 9:1363–1367) nucleocapsid gene is cloned in the plant transformation vector pBIN19 (Bevan, M. (1984) Nucl. Acids Res. 12(22):8711–8721) containing the NPTII selection gene. Transformants, selected for kanamycin resistance, are analyzed for both the copy number of the TSWV transgene by Southern blotting hybridization and for expression of the TSWV nucleocapsid gene by specific ELISA assays. Transformants, containing one single copy of the TSWV nucleocapsid gene, are selfed and tested for gene expression stability in the successive generations by ELISA analysis. A genomic cosmid DNA library is constructed from purified tomato chromosomal DNA, isolated from a stable transgenic S3 line using the restriction endonuclease Mbol.

Colony hybridization screening with the TSWV nucleocapsid gene as probe results in the identification of clones carrying the transgene; using chromosome walking techniques (Maniatis 1989), 100 kbp regions upstream and 100 kpb regions downstream of the transgene are identified and further characterized. This 200 kbp region includes part of an euchromatin ("open") loop; most probably this region includes a complete euchromatin loop, as the sizes of average chromatin loops are 80–90 kbp (Jackson et al. 1990). Subclones of this 200 kbp region are tested for specific nuclear matrix binding in the nuclear matrix MAR binding system, as described in Example 9. Several tomato chromosomal DNA fragments are Identified as specific MAR DNA sequences.

Example 14

Isolation of Plant MAR DNA Sequences Flanking 5' and 3' of Nuclear Genes

A genomic cosmid DNA library is constructed (using the restriction endonuclease Mbol) from purified tomato chromosomal DNA. Colony hybridization screening results in a clone containing the tomato plastocyanin gene with about 20 kbp flanking region from both sides. The 5' region is subcloned and tested for specific binding in the nuclear matrix MAR binding system as described in Example 9. An approximately 1 kbp 5' upstream tomato chromosomal DNA subfragment is identified as a specific MAR DNA sequence.

Example 15

Identification of Hypersensitive Chromosomal DNA Regions

Chromatin is organized in topologically constrained DNA loops by the anchoring of specific MAR sequences to the external (shell) and internal nuclear matrix. Loops carrying potential active genes (called dispersed euchromatin) are thought to contain regions which are accessible for transcription factors, RNA polymerases and other components required for transcription, whereas inactive loop (regions) (called condensed heterochromatin) are inaccessible. A transgene in a stable transgenic (plant) line is supposed to be integrated in an at least partly dispersed, open euchromatin loop region, which is transcriptionally active. The accessibility of such chromatin loop regions carrying active (trans) genes is reflected by an increased sensitivity to nuclease digestion as compared to inactive chromatin loop regions (Weintraub and Groudine, 1976). Molecular mechanisms underlying the controlling of open/dispersed or closed/condensed loop (regions) are yet not understood. However, certain cis-acting enhancer-like DNA fragments (called LOR—locus control region (Felsenfeld, G. (1992) Nature 355:219–223) are supposed to act as open < > close switches/regulators for the chromatin conformation in loop regions. Differentiation is a process of tissue-specific differential gene expression by means of inactivating or closing euchromatin regions into heterochromatin regions. Hypersensitive chromosomal DNA regions are defined as DNA regions showing an increased sensitivity toward nuclease digestion. Such hypersensitive DNA regions contain cis-acting regulator sequences like LCR sequences. Therefore screening for DNAse I hypersensitive DNA regions is a tool for preselecting chromatin conformation-regulating cis-acting elements.

Protoplasts are isolated as described in Example 8, with the modification that the cell wall degradation enzymes are applied in (lower) range concentrations, resulting in permeable cells which are intermediate forms between in vivo cells and protoplasts. Cells/protoplasts are washed in W5 medium twice, followed by resuspension in nuclease buffer (0.05 M Tric-HCl, pH 7.8, 5 mM $MgCl_2$, 0.01 M 2-mercaptoethanol, 10 $\mu$g/ml BSA). Cells are treated with varying concentrations of DNAseI ($10^{-3}$–$10^{-5}$ U/ml) for 10' at room temperature. DNA is isolated using a standard phenol/chloroform method, digested with appropriate restriction enzymes and blotted to Hybond $N^+$. Hybridizations are carried out with probes derived from the 200 kbp genomic region surrounding the stable TSWV nucleocapsid gene isolated from a stable tomato transgenic line (described in Example 12). Hypersensitive regions (carrying chromatin conformation regulating cis-acting elements) are identified as those regions which show a decrease in amount of probe able to hybridize with the expected DNA restriction fragment when a series of increasing DNAse I concentrations is applied to the permeable tomato cells. Alternatively, identification of HR can also be performed by analyzing additional hypersensitive related DNA subfragments essentially as described by Forrester, W. C. et al. (1990) Genes and Development 4:1637–1649.

Example 16

Transgene Instability in Lettuce

From a typical Agrobacterium-mediated transformation experiment, sixteen independent S1 progeny lines are obtained that express the introduced transgene: the TSWV nucleoprotein gene cassette (a schematic representation of the T-DNA is shown in FIG. 4). Individual S1 progeny plants accumulating the TSWV nucleoprotein are maintained and self-pollinated. The resulting S2 progeny lines representing the 16 transformant lines, are again analyzed for accumulation of the TSWV nucleoprotein by ELISA analysis, revealing the segregation ratio of the transgene. At this time, abnormal, nonMendelian segregation ratios and "silencing" of gene expression are observed in approximately 50% of the transformant lines, Indicating instability of transgene expression. Stable, "homozygous" S2 populations, in which the transgene has been "fixed" in the homozygous state are identified for only six transformant lines.

Southern blot analysis of "unstable" transformant lines that exhibit abnormal segregation ratios at the expression level, demonstrates that the transgene segregates normally at the DNA level within the S2 population. Nine individual S2 plants from two unstable S2 lines (6A-7 and 26-11), are analyzed for presence and expression of the transgene by means of Southern blot analysis and ELISA analysis, respectively. As shown in FIG. 7, a correlation between presence and expression of the transgene cannot be observed (plant numbers that accumulate the TSWV nucleoprotein as determined in the ELISA assay have been encircled; digestion with XbaI releases the complete TSWV nucleoprotein gene cassette of 1.6 kb, while digestion with HindIII generates border fragments correlated with the number of T-DNA copies integrated into the genome). The transgene itself segregates "normally" at the DNA level; only two out of the nine individuals analyzed do not carry the transgene, but some plants that do carry the transgene do not express the transgene, which illustrates the instability of transgene expression.

Southern blot analysis of a number of nonexpressor lines digested with XbaI demonstrates the presence of the transgene, but none of these S2 lines accumulate TSWV nucleoprotein. Again a correlation between the presence and expression of the transgene cannot be demonstrated. A few of these S2 lines still accumulate the nucleoprotein gene product in the S1 population (transformant lines 11 and 21), illustrating the progressive "silencing" of transgene expression over generations.

Instability of transgene expression has also been observed in two transformant lines carrying the bar gene from streptomyces hygroscopicus which confers resistance to phosphinothricine, the active compound in a number of commercial herbicides. Herbicide treatment of S1 and S2 progeny populations revealed non-Mendelian segregation ratios and fixation of the herbicide resistance trait in homozygous lines could not be accomplished.

Example 17

Transgene Instability in Tomato

In tomato a similar example of transgene instability is observed upon introduction of the TSWV nucleoprotein gene cassette. As in the case of lettuce, the first signs of "silencing" of transgene expression are encountered during ELISA analyses of the progeny populations revealing abnormal, non-Mendelian segregation ratios. Combined ELISA and southern blot analysis of nine individual S2 progeny plants (transformant line 27-5) descending from one primary transformant result in the identification of certain plant individuals that carry an inactivated transgene. Digestion with XbaI releases the complete TSWV nucleoprotein gene cassette of 1.6 kb, while digestion with HindIII generates border fragments, the number of which correlates with the number of T-DNA copies integrated into the genome. Apparently, the transgene itself segregates normally at the DNA level; only one-third of the individuals analyzed have "lost" the transgene through segregation, but others may harbor transgenes that have been inactivated, resulting in abnormal segregation ratios at the protein level.

Detailed analysis of individual tomato plants that descend from unstable transformant lines provided more insight in the phenomenon of instability. Upon sampling of leaf material differing in age from one and the same plant ELISA-positive as well as ELISA-negative samples were identified, resulting in a 'mosaic' pattern of transgene expression throughout the plant. A correlation between transgene inactivation and leaf age could not be observed. In vitro regeneration of tomato shoots from explants taken from 'silenced' transformants resulted in partial reactivation of transgene expression, in that ELISA-positive as well as ELISA-negative shoots could be identified. This result proves the possiblitity of reactivating 'silenced' transgenes through tissue culture.

Example 18

Stabilization of Gene Expression Over Generations Using MAR Sequences

To assess the effects of MAR sequences as boundary elements on gene expression over generations, a number of "T-DNA" constructs is transformed to tomato and lettuce, in which the NPTII selection marker and the TSWV nucleoprotein gene cassette are flanked by MAR sequences isolated from rat, soybean and tomato (pMARr, pMARs and pMARt, respectively). A schematic representation of these T-DNAs is shown in FIG. 5. The pMARc construct carries boundary elements consisting of random DNA sequences (e.g., vector DNA) of about equal length to the MAR elements, but that do not exhibit any affinity to plant nuclear matrices.

Upon Agrobacterium-mediated transformation of tomato and lettuce, primary transformants accumulating TSWV nucleocapsid protein are analyzed for their T-DNA copy number through Southern blot analysis. Only transformants that carry a single copy of the T-DNA are maintained and self-pollinated. From the resulting S1 progeny population, ten individual plants expressing the nucleoprotein transgene are once more self-pollinated to produce S2 lines. Nonsegregating S2 lines in which the transgene has been "fixed" in the homozygous state, are identified by means of ELISA analysis for accumulation of TSWV nucleoprotein. These "homozygous" S2 lines are maintained by repeated selfing and monitored for stability of transgene expression over successive generations. In comparison to the pMARc construct, the percentage of stable pMARs and pMARt transformant lines after eight generations is significantly higher, which illustrates the stabilizing effect that these MAR sequences exert on transgene expression in tomato. In case of the pMARt construct the progressive transgene inactivation as observed for the pMARc vector over successive generations is almost completely prevented. To a lesser extent the same phenomenon is observed for the heterologous rat MAR element, which is not as efficient as the plant-derived MAR sequences in stabilizing transgene expression, resulting in an intermediate percentage of stable transformants.

In lettuce both plant derived MAR sequences perform equally well. The tomato as well as the soybean MAR reduce the instability of transgene expression in lettuce as exemplified by the pMARc transformant lines. Apparently, plant-derived MAR sequences can be used in heterologous transformation systems to stabilize transgene expression over generations.

What is claimed:

1. An isolated nucleic acid molecule comprising an exogenous gene, the exogenous gene comprising a promoter sequence and a coding sequence and at least one DNA segment comprising a sequence selected from the group consisting of SEQ ID NO:1, SEQ ID NO:2, SEQ ID NO:3, SEQ ID NO:4 and SEQ ID NO:5, wherein the DNA segment is located in a 5'-flanking region upstream of the promoter sequence.

2. The isolated nucleic acid molecule according to claim 1 further comprising a second DNA segment in a 3'-flanking region of the exogenous gene, said second DNA segment having a sequence selected from the group consisting of SEQ ID NO:1, SEQ ID NO:2, SEQ ID NO:3, SEQ ID NO:4 and SEQ ID NO:5 wherein the 3'-flanking region of the exogenous gene is down stream of the coding sequence and may or may not lie down stream of a polyadenylation signal where a polyadenylation signal is present.

3. A plant transformation vector, said vector comprising the isolated nucleic acid molecule of claim 1.

4. A plant transformation vector comprising the isolated nucleic acid molecule of claim 2.

5. A vector according to claim 3 wherein said exogenous gene comprises more than one coding region, each coding region having its own promoter.

6. A vector according to claim 5 comprising a first and second DNA segment, each DNA segment having a sequence selected from the group consisting of SEQ ID NO: 1, SEQ ID NO:2, SEQ ID NO:3, SEQ ID NO:4 and SEQ ID NO:5, wherein, the first DNA segment is situated 5' to both coding regions and both promoter sequences and the second DNA segment is situated between said coding regions and upstream of the promoter sequence of the subsequent coding region.

7. A vector according to claim 5 comprising a first and second DNA segment, each DNA segment having a sequence selected from the group consisting of SEQ ID NO: 1, SEQ ID NO:2, SEQ ID NO:3, SEQ ID NO:4 and SEQ ID NO:5, wherein, the first DNA segment is situated 5' to both coding regions and the promoter sequence of each coding sequence and the second DNA segment is situated 3' to both coding regions.

8. A method for transforming a plant cell comprising introducing into said plant cell the isolated nucleic acid of claim 1.

9. A method for transformation of a plant cell comprising introducing into said plant cell the isolated nucleic acid of claim 2.

10. A method according to claim 8 wherein the exogenous gene comprises more than one coding region.

11. A method for expressing an exogenous gene in a plant wherein said exogenous gene comprises more than one coding region, comprising inserting between the coding regions a DNA segment comprising a sequence selected from the group consisting of SEQ ID NO:1, SEQ ID NO:2, SEQ ID NO:3, SEQ ID NO:4 and SEQ ID NO:5.

12. The isolated DNA molecule according to claim 1, wherein the DNA segment comprises a fragment of SEQ ID NO:5 comprising at least 0.59 Kb contiguous bases of the sequence set forth in SEQ ID NO:5.

13. The plant transformation vector according to claim 3, wherein the at least one DNA segment comprises a fragment of SEQ ID NO:5 comprising at least 0.59 Kb contiguous bases of the sequence set forth in SEQ ID NO:5.

14. The method of claim 8, wherein the at least one DNA segment comprises a fragment of SEQ ID NO:5 comprising at least 0.59 Kb contiguous bases of the sequence set forth in SEQ ID NO:5.

* * * * *